(12) United States Patent
Ganssle et al.

(10) Patent No.: US 10,241,172 B2
(45) Date of Patent: Mar. 26, 2019

(54) REFOCUSSING PULSE HAVING AN INCREMENTAL PHASE

(71) Applicant: Halliburton Energy Services, Inc., Houston, TX (US)

(72) Inventors: Paul Ganssle, Houston, TX (US); Shriram Sarvotham, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 702 days.

(21) Appl. No.: 14/780,348

(22) PCT Filed: Dec. 13, 2013

(86) PCT No.: PCT/US2013/075148
§ 371 (c)(1),
(2) Date: Sep. 25, 2015

(87) PCT Pub. No.: WO2015/088566
PCT Pub. Date: Jun. 18, 2015

(65) Prior Publication Data
US 2016/0054412 A1    Feb. 25, 2016

(51) Int. Cl.
*G01R 33/50*      (2006.01)
*G01N 24/10*      (2006.01)
(Continued)

(52) U.S. Cl.
CPC .......... *G01R 33/50* (2013.01); *G01N 24/081* (2013.01); *G01N 24/10* (2013.01); *G01R 33/54* (2013.01);
(Continued)

(58) Field of Classification Search
CPC ...... G01N 24/081; G01N 24/10; G01R 33/46; G01R 33/50; G01R 33/54; G01R 33/5617; G01R 33/60; G01V 3/32
See application file for complete search history.

(56) References Cited

U.S. PATENT DOCUMENTS 6,121,774 A *   9/2000   Sun ...................... G01N 24/081
                                                      324/300
6,163,453 A      12/2000   Hou et al.
(Continued)

OTHER PUBLICATIONS

Baltisberger et al., "Communication: Phase incremented echo train acquisition in NMR spectroscopy," The Journal of Chemical Physics, vol. 136, 211104, published Jun. 4, 2012, 8 pages.
(Continued)

*Primary Examiner* — Jay Patidar
(74) *Attorney, Agent, or Firm* — Benjamin Fite Parker Justiss, P.C.

(57) ABSTRACT

An example pulse sequence for performing phase coherence order selection within a single transient acquisition includes an excitation pulse with a tip angle of 90° and phase φA, followed by a train of N refocusing pulses with tip angles of 180°, with the center of the first refocusing pulse occurring time τ after the center of the excitation pulse, and the center of the $n^{th}$ refocusing pulse occurring at time (2n+1)τ after the center of the excitation pulse. This causes a train of echoes to form at times 2nτ after the center of the excitation pulse. In this example, the first refocusing pulse has phase φB, where |φB−φA|=90°, and each successive refocusing pulse (304) has a phase φδ greater than the last refocusing pulse. This incremental change in pulse phase over the course of the echo train has the effect of aiabatically "dragging" the echo phase around the unit circle in a predictable manner corresponding to the phase coherence order of the relevant signals.

45 Claims, 20 Drawing Sheets

(51) Int. Cl.
*G01V 3/32* (2006.01)
*G01N 24/08* (2006.01)
*G01R 33/54* (2006.01)
*G01R 33/46* (2006.01)
*G01R 33/561* (2006.01)
*G01R 33/60* (2006.01)

(52) U.S. Cl.
CPC .............. *G01V 3/32* (2013.01); *G01R 33/46* (2013.01); *G01R 33/5617* (2013.01); *G01R 33/60* (2013.01)

(56) References Cited

U.S. PATENT DOCUMENTS

| | | | |
|---|---|---|---|
| 6,204,663 | B1 | 3/2001 | Prammer |
| 6,429,654 | B1 | 8/2002 | Itskovich et al. |
| 6,518,757 | B1 | 2/2003 | Speier |
| 6,570,381 | B1 * | 5/2003 | Speier .................. G01N 24/081 324/303 |
| 6,690,167 | B2 | 2/2004 | Reiderman et al. |
| 7,034,529 | B2 | 4/2006 | Blanz et al. |
| 2002/0140426 | A1 | 10/2002 | Liu et al. |
| 2004/0008027 | A1 * | 1/2004 | Prammer ............. G01N 24/081 324/303 |
| 2004/0066192 | A1 | 4/2004 | Heidler |
| 2005/0020585 | A1 | 1/2005 | Cosford et al. |
| 2005/0124396 | A1 | 6/2005 | Brems et al. |
| 2005/0231198 | A1 * | 10/2005 | Beard .................. G01N 24/081 324/303 |
| 2005/0248342 | A1 | 11/2005 | Rottengatter et al. |
| 2007/0032956 | A1 * | 2/2007 | Blanz ...................... G01V 3/32 702/14 |
| 2007/0222443 | A1 | 9/2007 | Blanz |
| 2012/0319689 | A1 * | 12/2012 | Ichinose ............ G01R 33/3664 324/322 |

OTHER PUBLICATIONS

International Search Report/Written Opinion issued by Korean Intellectual Patent Office for PCT/US2013/075148 dated Sep. 1, 2014; 23 pages.

* cited by examiner

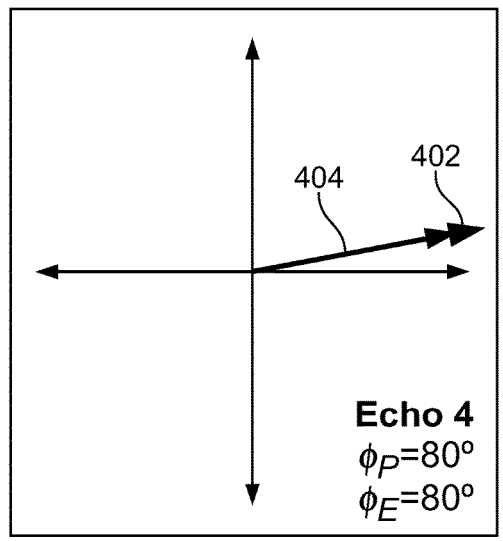
FIG. 4D
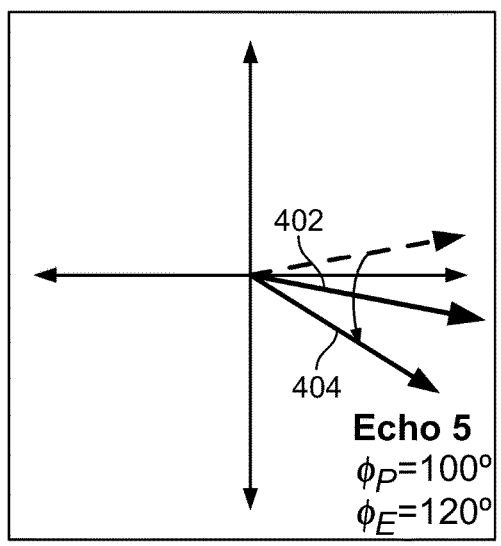 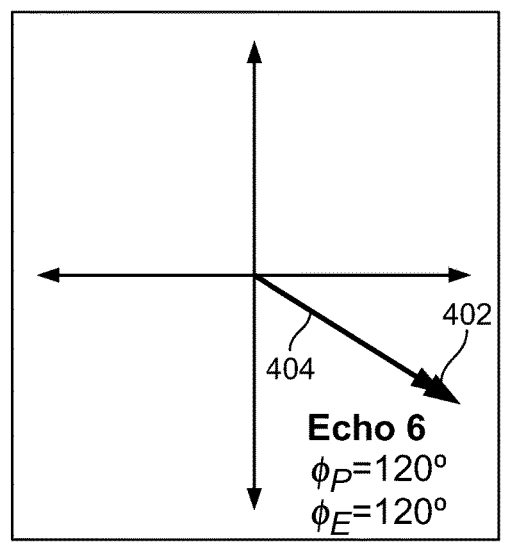
FIG. 4E  FIG. 4F

REFOCUSSING PULSE HAVING AN INCREMENTAL PHASE

This application is a U.S. National Stage of International Application No. PCT/US/2013/075148, filed Dec. 13, 2013.

TECHNICAL FIELD

This invention relates to magnetic resonance measurements, and more particularly to pulse sequences used therein.

BACKGROUND

In the field of nuclear magnetic resonance (NMR), spin echo-based sequences are used to measure many material properties such as relaxivity and diffusivity. These sequences are used in a variety of contexts such as medical imaging, chemical analysis and particularly the characterization of heterogeneous media. Spin echo sequences are particularly valuable when making "ex-situ" measurements, as they tend to be robust in the presence of strong gradients. These sequences are often used in the field of logging (e.g., wireline logging, logging while drilling (LWD) and measurement while drilling (MWD), NMR tools have been used to explore the subsurface based on magnetic interactions with subsurface material. Some downhole NMR logging tools include a magnet assembly that produces a static magnetic field, and an antenna assembly that generates radio-frequency (RF) control signals and detects magnetic resonance phenomena in the subsurface material.

DESCRIPTION OF DRAWINGS

FIGS. 4A-F are diagrams showing an example relationship between pulse phases and the phase of the resulting echoes.

Like reference symbols in the various drawings indicate like elements.

DETAILED DESCRIPTION

Nuclear magnetic resonance (NMR) is used in a variety of contexts, for instance in the fields of medicine and science for the characterization of heterogeneous media, or in the field of well logging (e.g., wireline logging, logging while drilling (LWD) and measurement while drilling (MWD)) to explore the subsurface of the earth. In the description below, embodiments are disclosed that relate to the use of NMR for well logging. However, it should be understood the implementations described here and not limited only to well logging applications, and may be broadly applicable to other applications in which NMR is used to characterize an unknown sample.

Figure 1A:
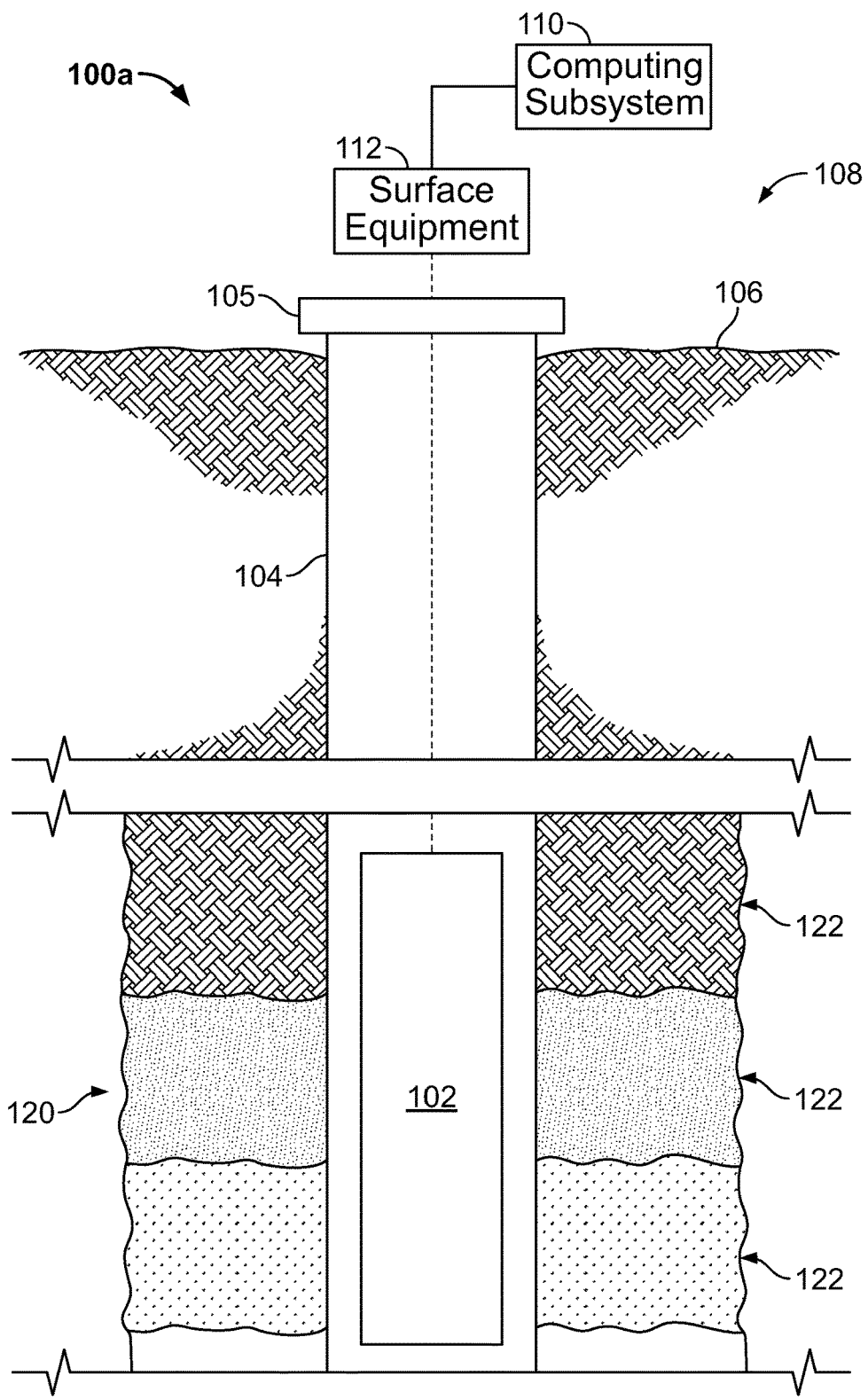
FIG. 1A is a diagram of an example well system.

Referring to FIG. 1A, NMR is used to observe properties of a well system 100a. The well system 100a includes an NMR logging system 108 and shows a subterranean region 120 beneath a ground surface 106. In general, well systems can include additional or different features that are not shown in FIG. 1A. For example, well systems may include additional drilling system components, wireline logging system components, etc.

The subterranean region 120 can include all or part of one or more subterranean formations or zones. The example subterranean region 120 shown in FIG. 1A includes multiple subsurface layers 122 and a wellbore 104 penetrated through the subsurface layers 122. The subsurface layers 122 can include sedimentary layers, rock layers, sand layers, or combinations of these other types of subsurface layers. One or more of the subsurface layers can contain fluids, such as brine, oil, gas, etc. Although the example wellbore 104 shown in FIG. 1A is a vertical wellbore, the NMR logging system 108 can be implemented in other wellbore orientations. For example, the NMR logging system 108 may be adapted for horizontal wellbores, slant wellbores, curved wellbores, vertical wellbores, or combinations of these.

The example NMR logging system 108 includes a logging tool 102, surface equipment 112, and a computing subsystem 110. In the example shown in FIG. 1A, the logging tool 102 is a downhole logging tool that operates while disposed in the wellbore 104. The example surface equipment 112 shown in FIG. 1A operates at or above the surface 106, for example, near the well head 105, to control the logging tool 102 and possibly other downhole equipment or other components of the well system 100. The example computing subsystem 110 can receive and analyze logging data from the logging tool 102. An NMR logging system can include additional or different features, and the features of an NMR logging system can be arranged and operated as represented in FIG. 1A or in another manner.

In some instances, all or part of the computing subsystem 110 can be implemented as a component of, or can be integrated with one or more components of, the surface equipment 112, the logging tool 102 or both. In some cases, the computing subsystem 110 can be implemented as one or more discrete computing system structures separate from the surface equipment 112 and the logging tool 102.

In some implementations, the computing subsystem 110 is embedded in the logging tool 102, and the computing subsystem 110 and the logging tool 102 can operate concurrently while disposed in the wellbore 104. For example, although the computing subsystem 110 is shown above the surface 106 in the example shown in FIG. 1A, all or part of the computing subsystem 110 may reside below the surface 106, for example, at or near the location of the logging tool 102.

The well system 100a can include communication or telemetry equipment that allow communication among the computing subsystem 110, the logging tool 102, and other components of the NMR logging system 108. For example, the components of the NMR logging system 108 can each include one or more transceivers or similar apparatus for wired or wireless data communication among the various components. For example, the NMR logging system 108 can include systems and apparatus for wireline telemetry, wired pipe telemetry, mud pulse telemetry, acoustic telemetry, electromagnetic telemetry, or a combination of these other types of telemetry. In some cases, the logging tool 102 receives commands, status signals, or other types of information from the computing subsystem 110 or another source. In some cases, the computing subsystem 110 receives logging data, status signals, or other types of information from the logging tool 102 or another source.

NMR logging operations can be performed in connection with various types of downhole operations at various stages in the lifetime of a well system. Structural attributes and components of the surface equipment 112 and logging tool 102 can be adapted for various types of NMR logging operations. For example, NMR logging may be performed during drilling operations, during wireline logging operations, or in other contexts. As such, the surface equipment 112 and the logging tool 102 may include, or may operate in connection with drilling equipment, wireline logging equipment, or other equipment for other types of operations.

In some implementations, the logging tool 102 includes a magnet assembly, which may be arranged to enhance the static magnetic field in a volume of interest. The logging tool 102 can also include one or more antenna assemblies. The antenna assemblies can produce polarized excitation in a subterranean volume and acquire a response from the volume by quadrature detection.

Figure 1B:
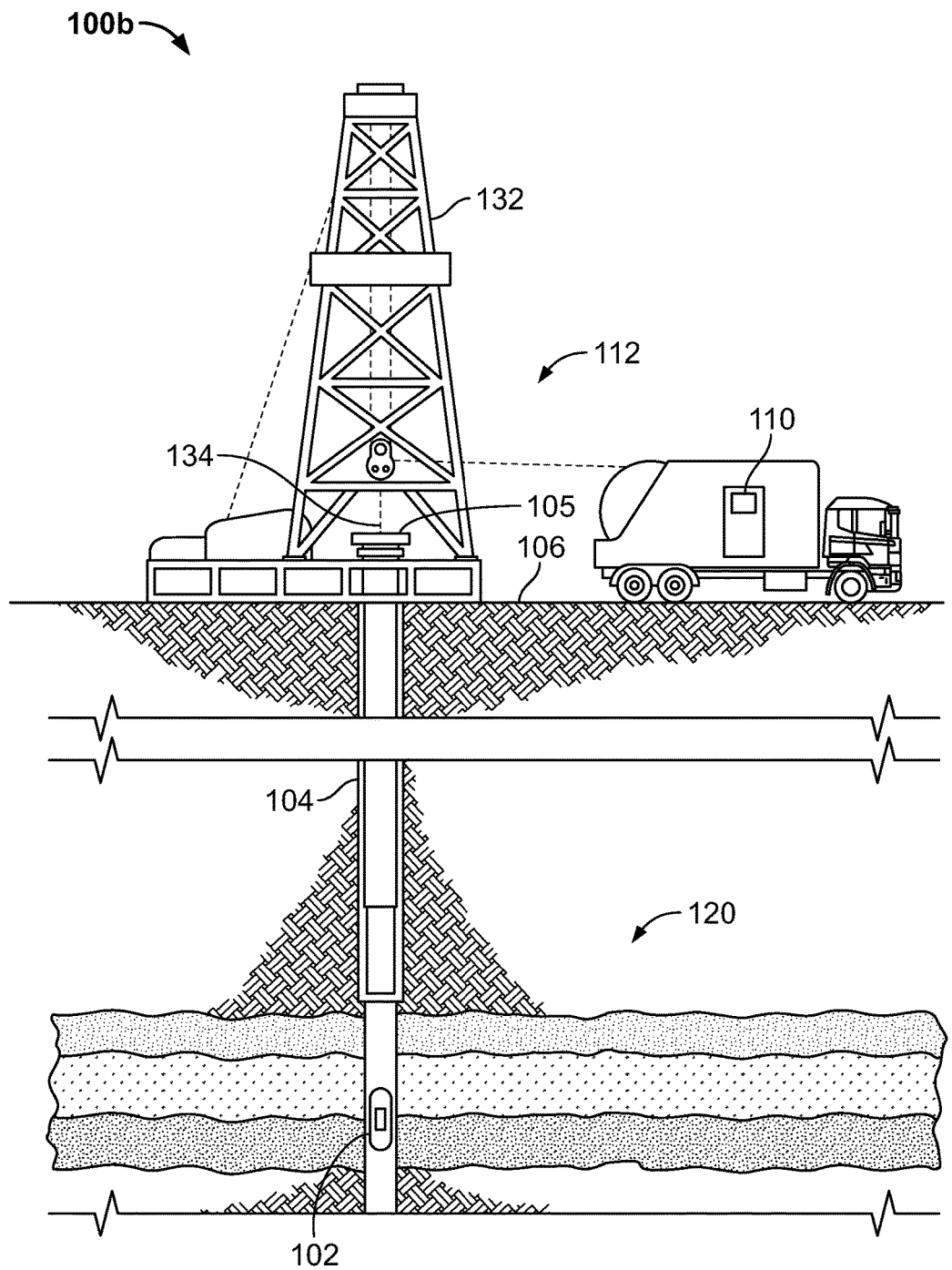
FIG. 1B is a diagram of an example well system that includes an NMR logging tool in a wireline logging environment.

In some examples, NMR logging operations are performed during wireline logging operations. FIG. 1B shows an example well system 100b that includes the NMR logging tool 102 in a wireline logging environment. In some example wireline logging operations, a the surface equipment 112 includes a platform above the surface 106 is equipped with a derrick 132 that supports a wireline cable 134 that extends into the wellbore 104. Wireline logging operations can be performed, for example, after a drilling string is removed from the wellbore 104, to allow the wireline logging tool 102 to be lowered by wireline or logging cable into the wellbore 104.

Figure 1C:
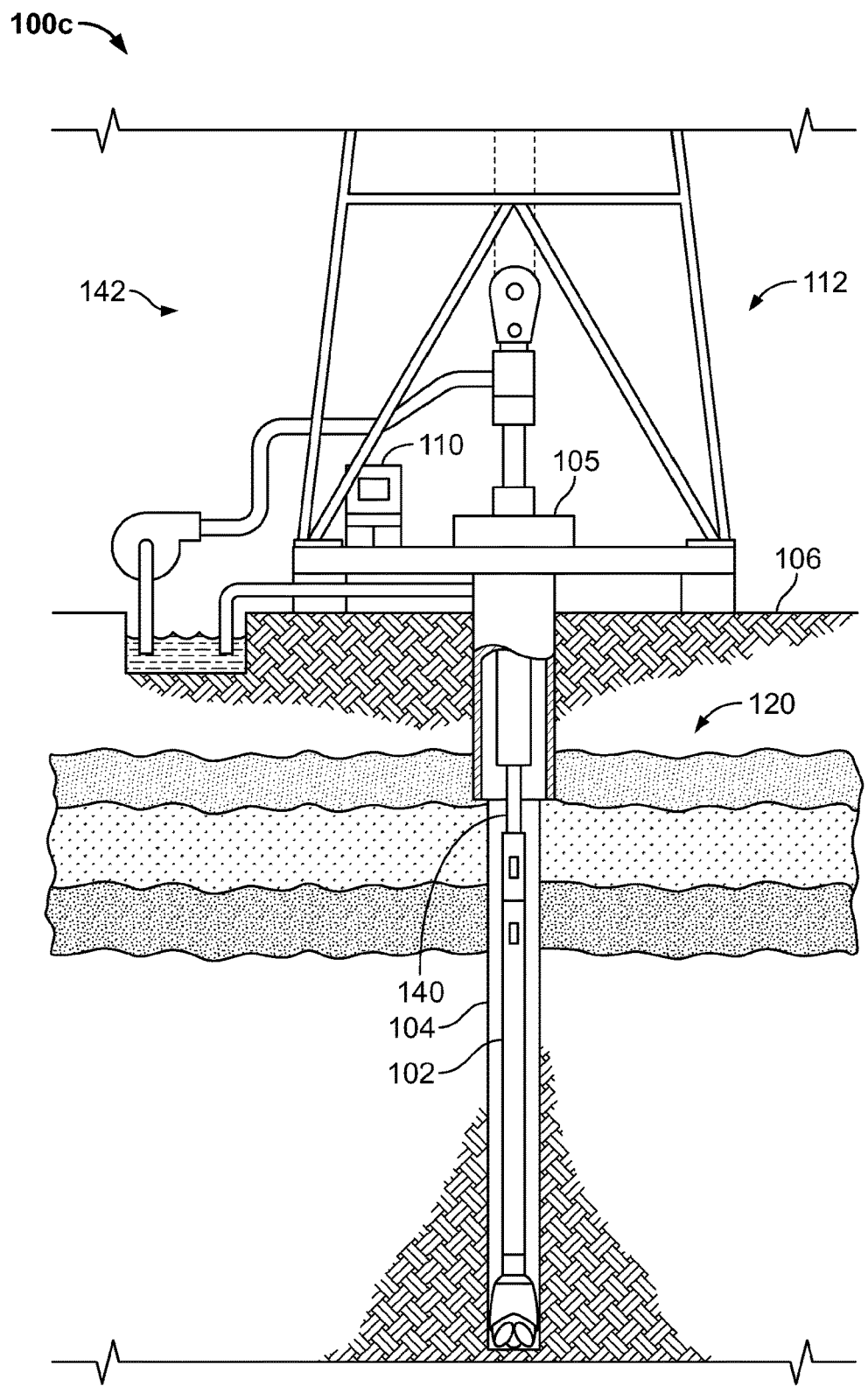
FIG. 1C is a diagram of an example well system that includes an NMR logging tool in a logging while drilling (LWD) environment.

In some examples, NMR logging operations are performed during drilling operations. FIG. 1C shows an example well system 100c that includes the NMR logging tool 102 in a logging while drilling (LWD) environment. Drilling is commonly carried out using a string of drill pipes connected together to form a drill string 140 that is lowered through a rotary table into the wellbore 104. In some cases, a drilling rig 142 at the surface 106 supports the drill string 140, as the drill string 140 is operated to drill the wellbore 104 to penetrate the subterranean region 120. The drill string 140 may include, for example, a kelly, drill pipe, a bottom hole assembly, and other components. The bottom hole assembly on the drill string may include drill collars, drill bits, the logging tool 102, and other components. The logging tools may include measuring while drilling (MWD) tools, LWD tools, and others.

In some example implementations, the logging tool 102 includes an NMR tool for obtaining NMR measurements from the subterranean region 120. As shown, for example, in FIG. 1B, the logging tool 102 can be suspended in the wellbore 104 by a coiled tubing, wireline cable, or another structure that connects the tool to a surface control unit or other components of the surface equipment 112. In some example implementations, the logging tool 102 is lowered to the bottom of a region of interest and subsequently pulled upward (e.g., at a substantially constant speed) through the region of interest. As shown, for example, in FIG. 1C, the logging tool 102 can be deployed in the wellbore 104 on jointed drill pipe, hard wired drill pipe, or other deployment hardware. In some example implementations, the logging tool 102 collects data during drilling operations as it moves downward through the region of interest during drilling operations. In some example implementations, the logging tool 102 collects data while the drilling string 140 is moving, for example, while it is being tripped in or tripped out of the wellbore 104.

In some example implementations, the logging tool 102 collects data at discrete logging points in the wellbore 104. For example, the logging tool 102 can move upward or downward incrementally to each logging point at a series of depths in the wellbore 104. At each logging point, instruments in the logging tool 102 perform measurements on the subterranean region 120. The measurement data can be communicated to the computing subsystem 110 for storage, processing, and analysis. Such data may be gathered and analyzed during drilling operations (e.g., during logging while drilling (LWD) operations), during wireline logging operations, or during other types of activities.

The computing subsystem 110 can receive and analyze the measurement data from the logging tool 102 to detect properties of various subsurface layers 122. For example, the computing subsystem 110 can identify the density, material content, or other properties of the subsurface layers 122 based on the NMR measurements acquired by the logging tool 102 in the wellbore 104.

In an example downhole NMR experiment, a static magnetic field, $B_0$, and second radio frequency (RF) magnetic field, $B_1$, are used to create and manipulate nuclear magnetization of a sample. NMR experiments can give insight to a variety of properties of the downhole environment, for example diffusion, viscosity, porosity (i.e., amount of fluid in an underground formation), and permeability, among others. These properties can be measured from the transient NMR response, which measures the $T_1$ recovery time (i.e., the recovery time of magnetization in the longitudinal direction) and $T_2$ decay time of the magnetization (i.e., the recovery time of magnetization in the transverse plane).

Figure 2:
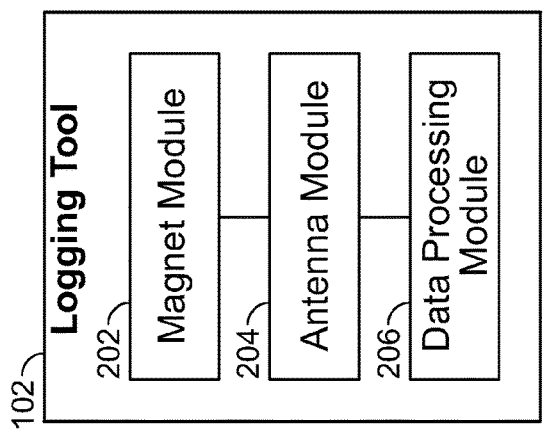
FIG. 2 is a diagram of an example logging tool.

The magnetic fields $B_0$ and $B_1$ can be generated in a variety of ways. For instance, referring to FIG. 2, magnetic fields $B_0$ and $B_1$ can be generated by an NMR logging tool 102. NMR logging tool 102 includes a magnet module 202, an antenna module 204, and a data processing module 206.

Magnet module 202 can be used to induce the magnetic field $B_0$ in an NMR experiment. For example, magnet module 202 can include a permanent magnetic or electro-magnetic that that directs magnetic flux outward from logging 102 in order to induce a magnetic field within the subterranean region 120.

Antenna module 204 can be used to induce an RF magnetic field $B_1$ in an NMR experiment, and can be used to measure the NMR signal in response to the induced fields. For example, antenna module 204 can include an antenna element defined by a path of electrically conductive material. When a current is applied to the antenna element, current flows through the path and induces a magnetic flux within the subterranean region 120. Current can be applied to induce a series of pulses (frequently referred to as "pulse sequences"), creating a time-varying magnetic field $B_1$ that aligns and/or otherwise manipulates the nuclear spins of the subterranean region 120.

In a similar manner, antenna module 204 can be used to detect changes in magnetism in the surrounding environment. For instance, in an example NMR experiment, nuclear magnetization within subterranean region 120 can be manipulated by a pulse sequence such that it initially aligns with the $B_0$ field, is tipped towards the $B_1$ field, and relaxes back towards the $B_0$ field. Antenna module 204 can be used to measure this NMR response through electromagnetic induction, and can be used to produce transient electric signals in response to the changing nuclear magnetism.

While magnetic fields $B_0$ and $B_1$ can be generated by the above described logging tool, these magnetic fields can also be generated in other ways. For instance, in some implementations, magnetic fields $B_0$ and $B_1$ can be generated by a separate tools that are used in conjunction to conduct an NMR experiment. In some implementations, magnetic field $B_0$ can be generated by a hyperpolarization method, or magnetic field $B_0$ may be an ambient field (e.g., the earth's magnetic field).

An NMR experiment can be designed to manipulate nuclear spins in a sample, so as to produce a particular frequency spectrum. Information regarding the sample can then be determined based on this frequency spectrum. However, in some circumstances, different components of an NMR signal may respond differently to changes in the phase of a pulse (i.e., the transmitter phase) and/or changes in the phase from which they are observed (i.e., the receiver phase), with many NMR signals containing components with various phase coherence values (i.e., the degrees to which the nuclear spins of a sample are coherent). As a result, the obtained spectrum may contain resonances other than those intended when the experiment was designed. In some circumstances, these spurious resonances can result in a variety of unwanted effects. For instance, in some cases, these resonances can introduce additional information to the spectrum that can obscure the wanted resonance peaks and lead to ambiguities of interpretation.

In some implementations, these unwanted resonances can be lessened through a procedure known as phase cycling, a method by which the transmitter and/or receiver phases are varied in an NMR experiment in order to eliminate unwanted signals on the basis of their phase response properties. Phase cycling can be used to separate out components of an NMR signal by their response to a change in transmitter and/or receiver phases, and can be used to remove undesirable resonances. In an example implementation, phase cycling can be used to selectively lessen or remove instrumental artifacts such as ringing, channel imbalances and signal offsets.

Phase cycling can be performed in a variety of ways. For example, in some circumstances, phase cycling can be achieved by repeating NMR experiments to produce several transient NMR responses. Each NMR experiment can be conducted with different values of the transmitter and receiver phase in order to separate out signals with different phase coherences. In an example, a set of NMR experiments can be designed such that each NMR experiment has a different transmitter and receiver phase pair. In this example, transmitter and receiver phases is selected such that the relative phase between each pair of phases remains the same, and such that when the NMR signals are averaged, components of an NMR signal with similar phase coherences are additively combined, while those of difference phase coherences cancel. In this manner, only signals of a particular phase coherence are isolated. In some implementations, instrumental artifacts are independent of the transmitter phase, while the NMR signal response depends linearly on the transmitter phase, and this technique can be used to isolate the NMR response signal from the instrumental artifacts. However, this approach may be undesirable in certain circumstances, as repeating an NMR experiment multiple times can increase the minimum duration of the experiment. This approach may also be problematic in circumstances, for instance when the logging tool is in motion during the NMR experiments, as each successive measurement is from a different position.

Figure 3:
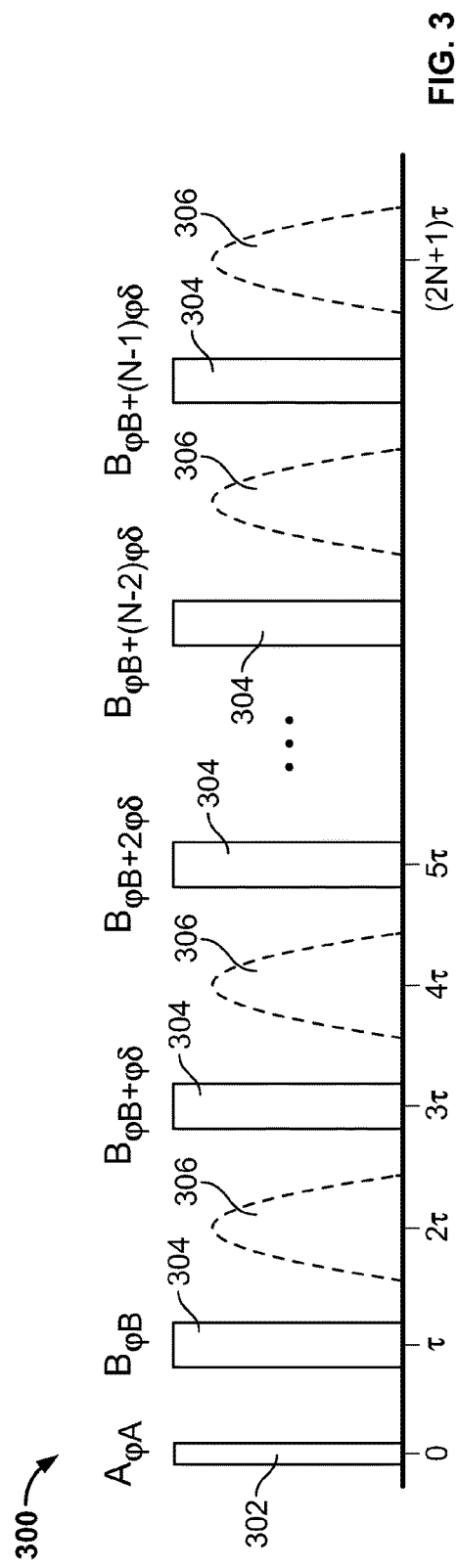
FIG. 3 is a diagram of an example pulse sequence for conducting a single-transient phase cycling.
Figure 4A:
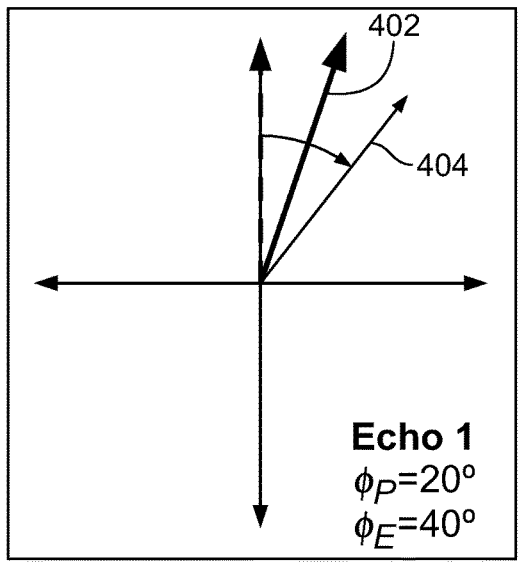
Figure 4B:
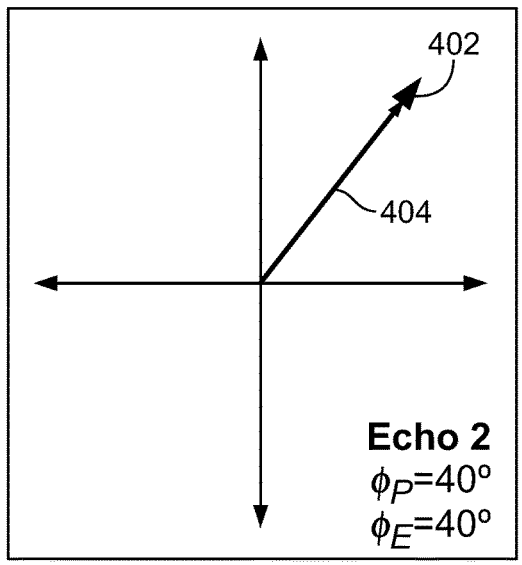
Figure 4C:
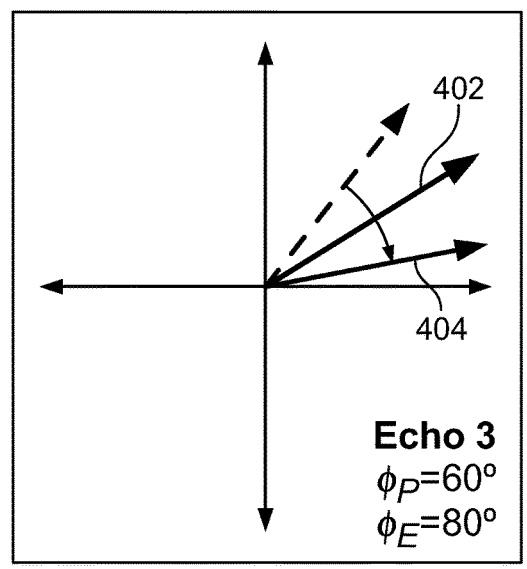

In some circumstances, phase cycling can be achieved by conducting a single NMR experiment to produce a single transient NMR response. An example pulse sequence 300 for conducting a single-transient phase cycling is shown in FIG. 3. Pulse sequence 300 is a variant of the Carr Purcell Meiboom Gill (CPMG) pulse sequence, and includes an excitation pulse 302 with a tip angle of 90° and phase $\phi_A$, followed by a train of N refocusing pulses 304 with tip angle 180°, with the center of the first refocusing pulse 304 occurring time $\tau$ after the center of the excitation pulse 302, and the center of the $n^{th}$ refocusing pulse occurring at time $(2n+1)\tau$ after the center of the excitation pulse 302. This causes a train of echoes 306 to form at times $2n\tau$ after the center of the excitation pulse.

In this example, the first refocusing pulse has phase $\phi_B$, where $|\phi_B-\phi_A|=90°$, and each successive refocusing pulse 304 has a phase $\phi_\delta$ greater than the last refocusing pulse. This incremental change in pulse phase over the course of the echo train has the effect of adiabatically "dragging" the echo phase around the unit circle in a predictable manner corresponding to the phase coherence order of the relevant signals. In an example, for an excitation pulse 302 with a tip angle of 90° and refocusing pulses 304 with tip angles of 180°, the phase of NMR signal with phase coherence of 1 at the $n^{th}$ echo is $n\phi_\delta+1$ on odd echoes, and $n\phi_\delta$ on even echoes, showing up in a quadrature signal as a wave with frequency $\phi/(4\pi\tau)$. In some implementations, in the presence of a gradient large enough that the bandwidth of the refocusing pulses 304 are selecting only a slice from the wider sample volume, echoes can form at phase $n\phi_\delta$ for all values of n. For example, referring to FIGS. 4A-F, when the pulse phase 402 of each refocusing pulse is incremented by 20°, the phase 404 of the resulting echoes is incremented by 40° for each odd-even pair of echoes. Accordingly, a linear phase increment of the refocusing pulses can have the effect of adiabatically dragging the phase of the echoes along with it.

After the NMR signal has been separated by phase coherence, unwanted artifacts can be removed. For example, in some implementations, the components of the signal can separated in Fourier space, allowing artifacts to be filtered away using a high-pass filter or bandpass filter. In some implementations, the phase of the receiver can be chosen during the experiment to follow the expected phase of the echoes, and a low-pass filter can be used to filter out unwanted components.

While the above example illustrates the use of a CPMG pulse sequence having an excitation pulse 302 with a tip angle of 90° and refocusing pulses 304 with tip angles of 180°, single-transient phase cycling can be performed in conjunction with other pulse sequences. For example, in some implementations, refocusing pulses 304 can have tip angles other than 180° (e.g., 90° and 135°). In some implementations, the excitation pulse 302 can have a tip angle other than 90°. In addition, the number of echoes can vary. For instance, in some implementations, pulse sequence 300 can have any number of echoes greater than two (e.g., three, four, five, six, and so forth).

Figure 5:
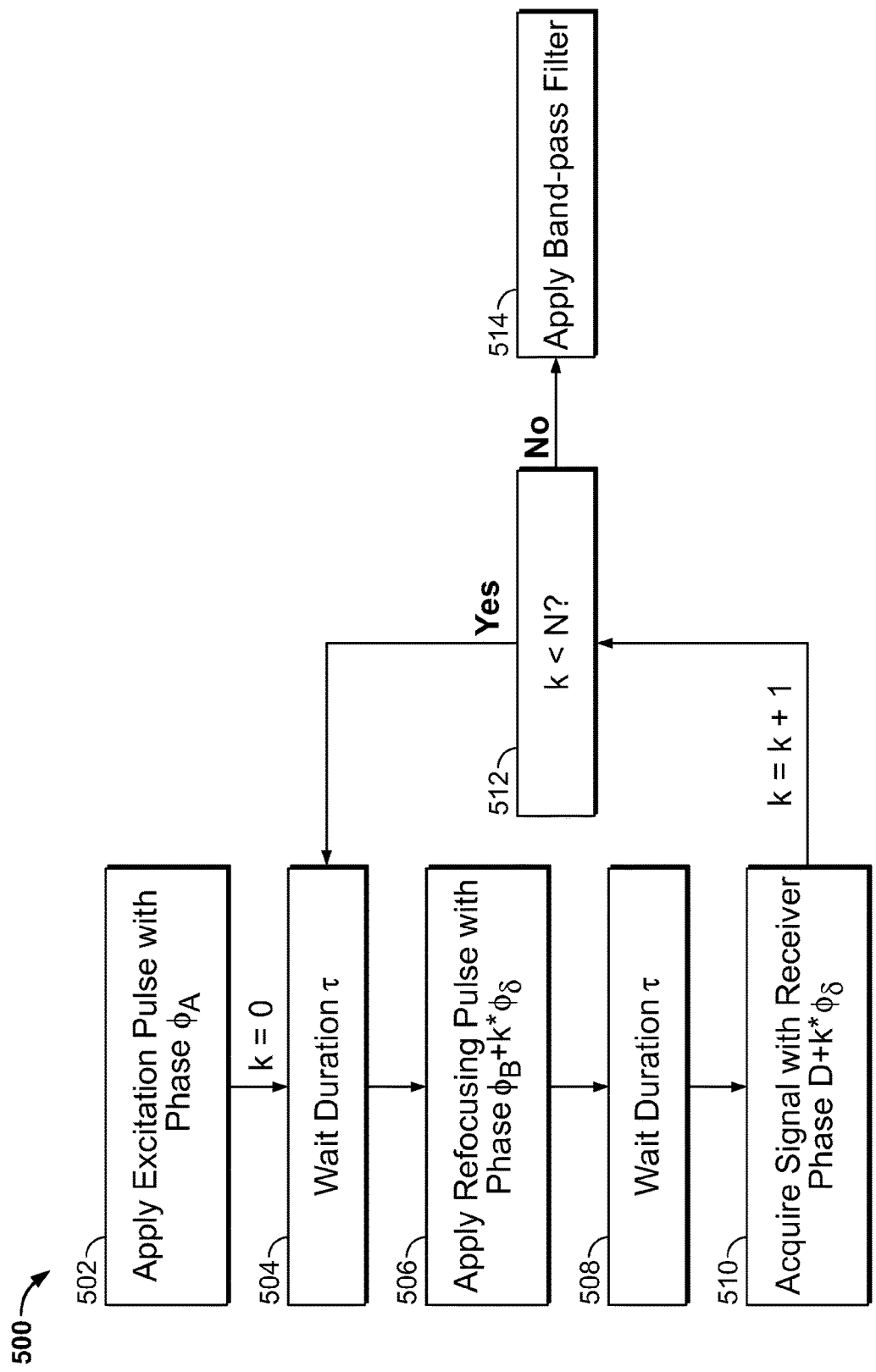
FIG. 5 is a diagram of an example method of single-transient phase cycling.

An example method 500 of single-transient phase cycling with N echoes is shown in FIG. 5. Method 500 begins after the nuclear spins of a particular sample volume have been polarized (e.g., by an applied magnetic field, hyperpolarization techniques, or natural polarization along an ambient field). First, an excitation pulse is applied having a phase $\phi_A$ (502), and an index k is set to zero. After waiting for a duration τ (504), a refocusing pulse with phase $\phi_B+k\phi_\delta$ is applied to the sample volume (506) in order to induce a corresponding echo. After waiting for a duration τ (508), the NMR signal corresponding to the induced echo is acquired with a receiver phase $\phi_C$, where $\phi_C=D+k\phi_\delta$ (510), where D is a constant. Constant D may be selected such that it is equal to the phase of the initial refocusing pulse (i.e., $D=\phi_B$), or equal to a phase value other than $\phi_B$.

After the NMR signal is acquired for the induced echo, the index k is incremented by one, and the value of k is compared to the desired number of echoes N (512). If k is less than N, steps 504, 506, 508, 510, and 512 are repeated. If k equals to N, then a band-pass filter is applied to the data (514), where the filter has a width selected in order to eliminate the artifacts from the desired NMR signal.

Figure 6A:
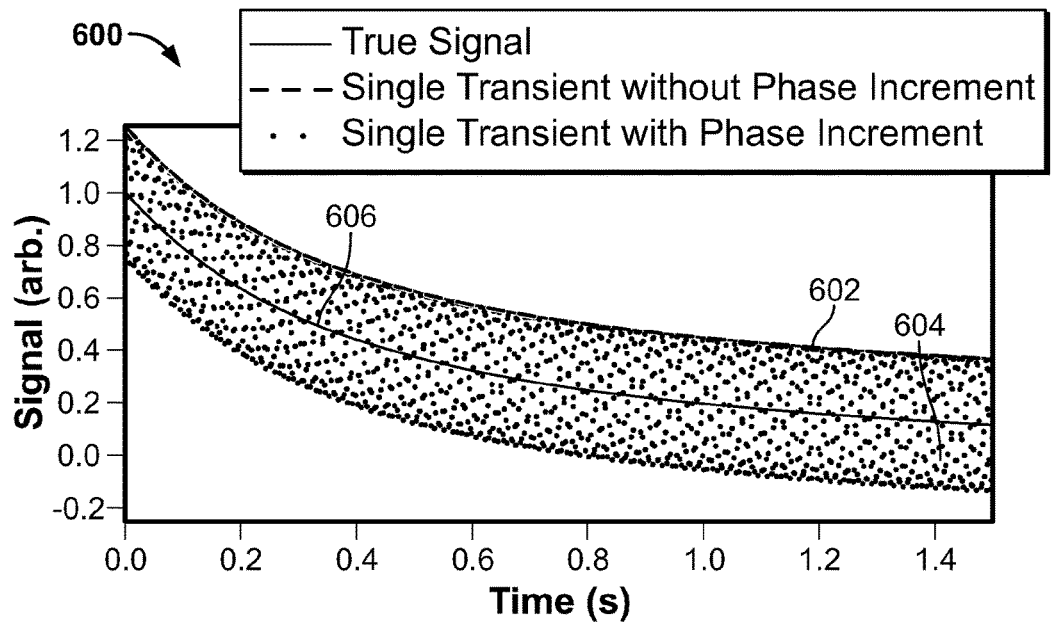
FIGS. 6A-B are plots of an example filtering process.
Figure 6B:
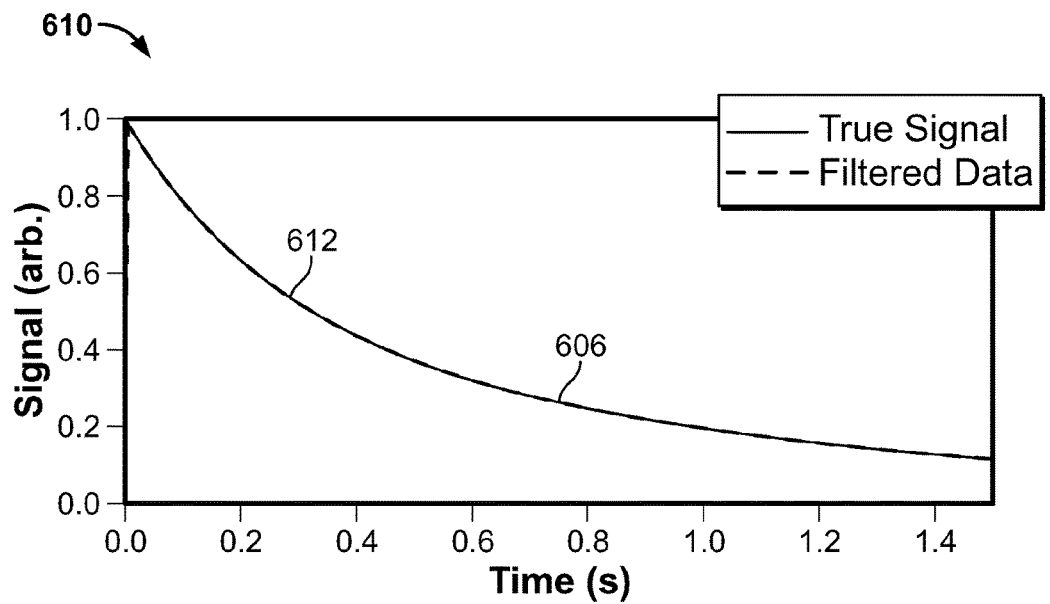

An example of filtering is shown in FIGS. 6A-B. Referring to FIG. 6A, plot 600 shows example simulated NMR signals obtained using a single-transient pulse sequence without phase increment (602), a single-transient pulse sequence with phase increment (e.g., as described above) (604), and the "true" signal (606), representing an ideal NMR signal without artifacts. In this simulated example, the signal obtained using a single-transient pulse sequence without phase increment (602) is offset from the true signal 606, and does not provide an accurate representation of the true signal. In addition, the signal obtained using a single-transient pulse sequence with phase increment (604) contains numerous frequency components (i.e., artifacts) that are not present in the true signal. Referring to plot 610 in FIG. 6B, by applying an appropriately selected low-pass filter to the signal obtained using a single-transient pulse sequence with phase increment 604, the resulting signal 612 can accurately represent the true signal 606.

Figure 7:
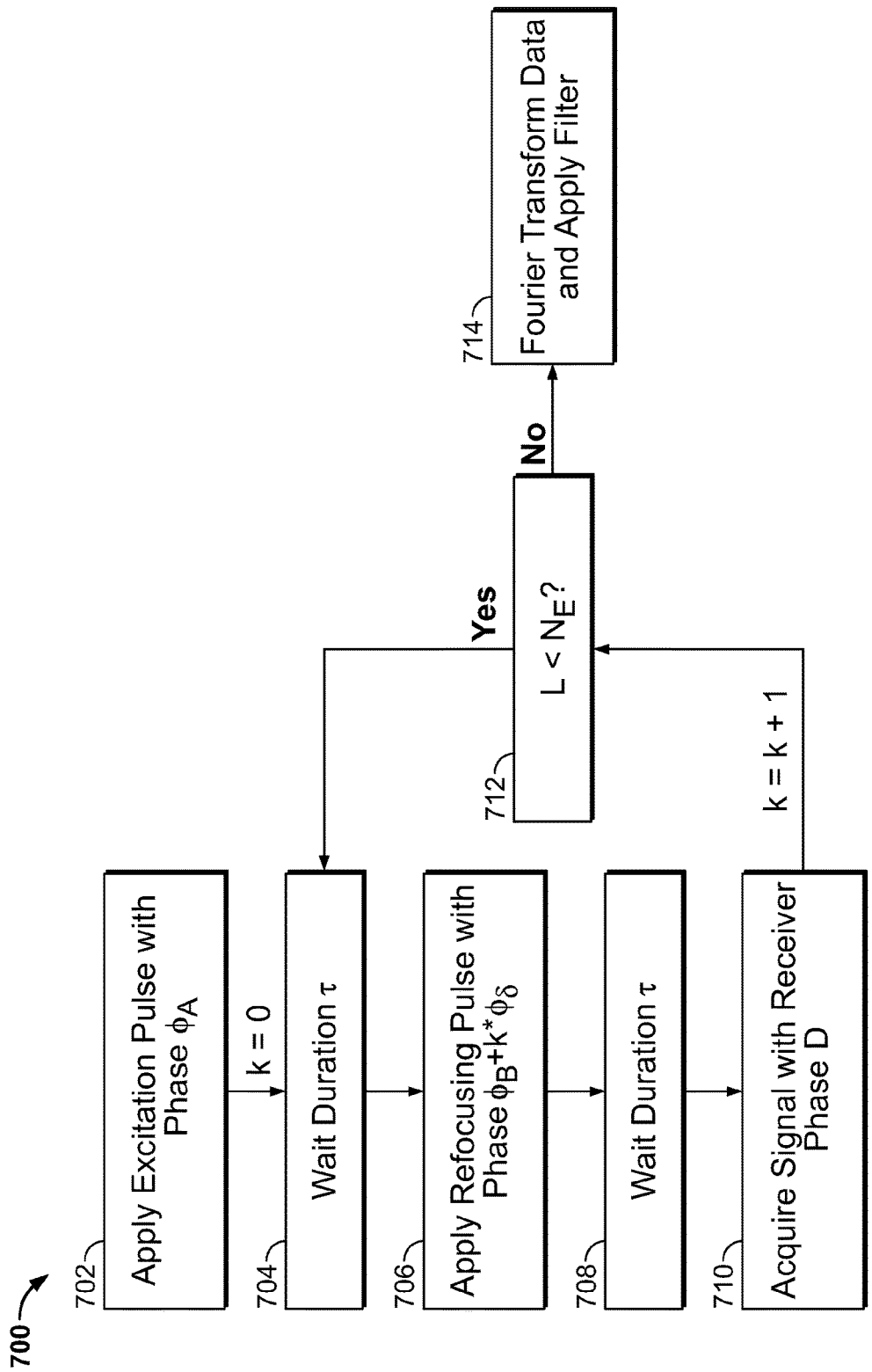
FIG. 7 is a diagram of another example method of single-transient phase cycling.

In the example method 500, the phase of the receiver can be chosen during the experiment to follow the expected phase of the echoes. However, this need not be the case. In some implementations, echoes acquired using a constant receiver phase, and the acquired signals components can be separated in Fourier space, allowing artifacts to be filtered away using a high-pass filter or bandpass filter. An example method 700 of single-transient phase cycling with N echoes is shown in FIG. 7. As above, method 700 begins after the nuclear spins of a particular sample volume have been polarized (e.g., by an applied magnetic field, hyperpolarization techniques, or natural polarization along an ambient field). First, an excitation pulse is applied having a phase $\phi_A$ (702), and an index k is set to zero. After waiting for a duration τ (704), a refocusing pulse with phase $\phi_B+k\phi_\delta$ is applied to the sample volume (706) in order to induce a corresponding echo. After waiting for a duration τ (708), the NMR signal corresponding to the induced echo is acquired with a receiver phase $\phi_C$ (710), where $\phi_C=D$ (510), where D is a constant. Constant D may be selected such that it is equal to the phase of the initial refocusing pulse (i.e., $D=\phi_B$), or equal to a phase value other than $\phi_B$.

After the NMR signal is acquired for the induced echo, the index k is incremented by one, and the value of k is compared to the desired number of echoes N (712). If k is less than N, steps 704, 706, 708, 710, and 712 are repeated. If k equals to N, then the data is Fourier transformed and an appropriate filter is selected to isolate the desired signal (714).

Figure 8:
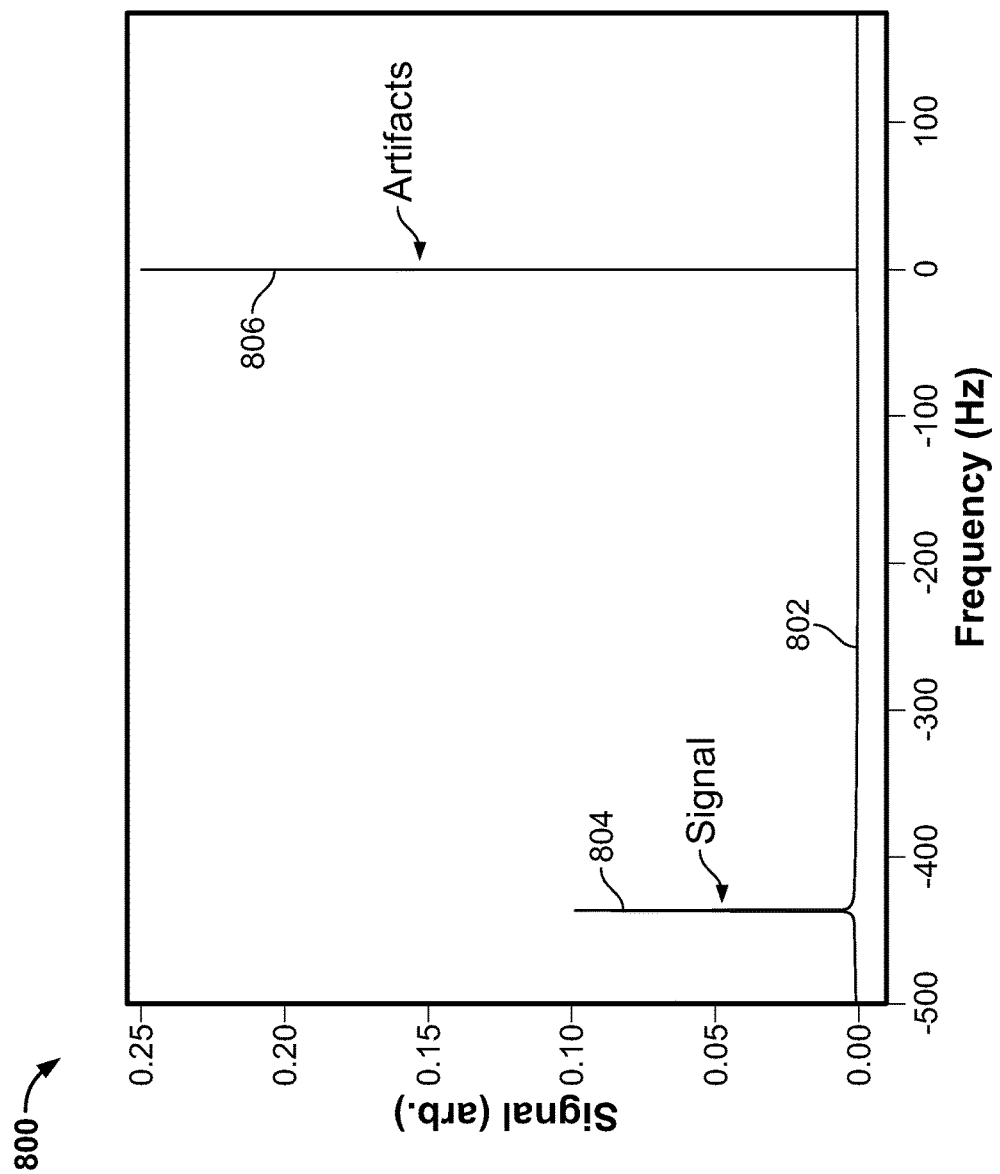
FIG. 8 is a plot of an example spectrum in the frequency domain.

An example of filtering is shown in FIG. 8, in which a plot 800 shows an example simulated spectrum 802 of a Fourier transformed NMR signal. The spectrum 802 contains a first signal peak 804, representing the desired signal, and a second signal peak 806, representing artifacts. An appropriate filter can be selected to isolate the desired signal from the artifacts, such that the resulting signal accurately represents the true signal.

Figure 9A:
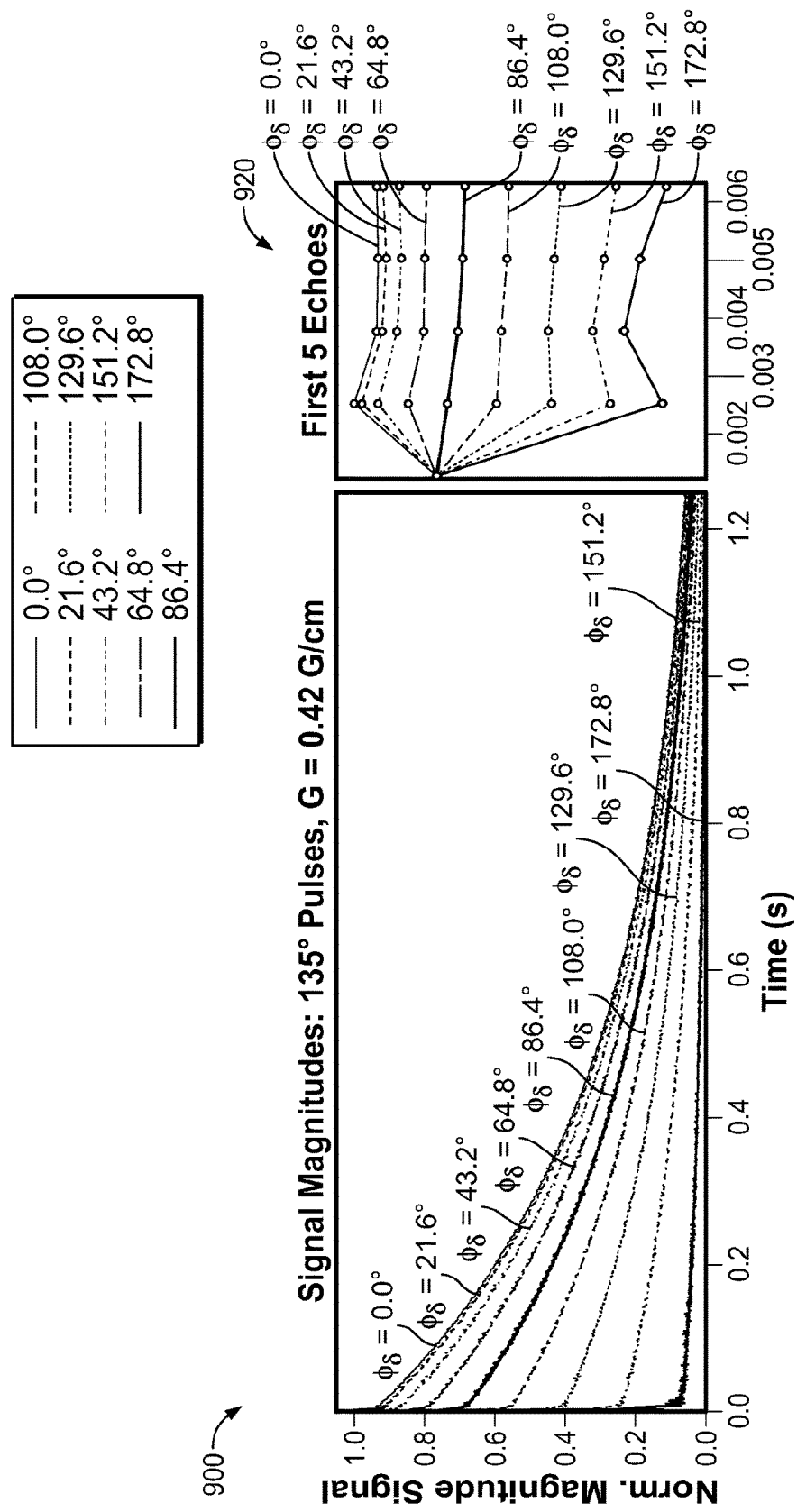
FIGS. 9A-B are plots that compare NMR signals induced by pulse sequences, each having a single excitation pulse and a train of refocusing pulses with different phase increments.
Figure 9B:
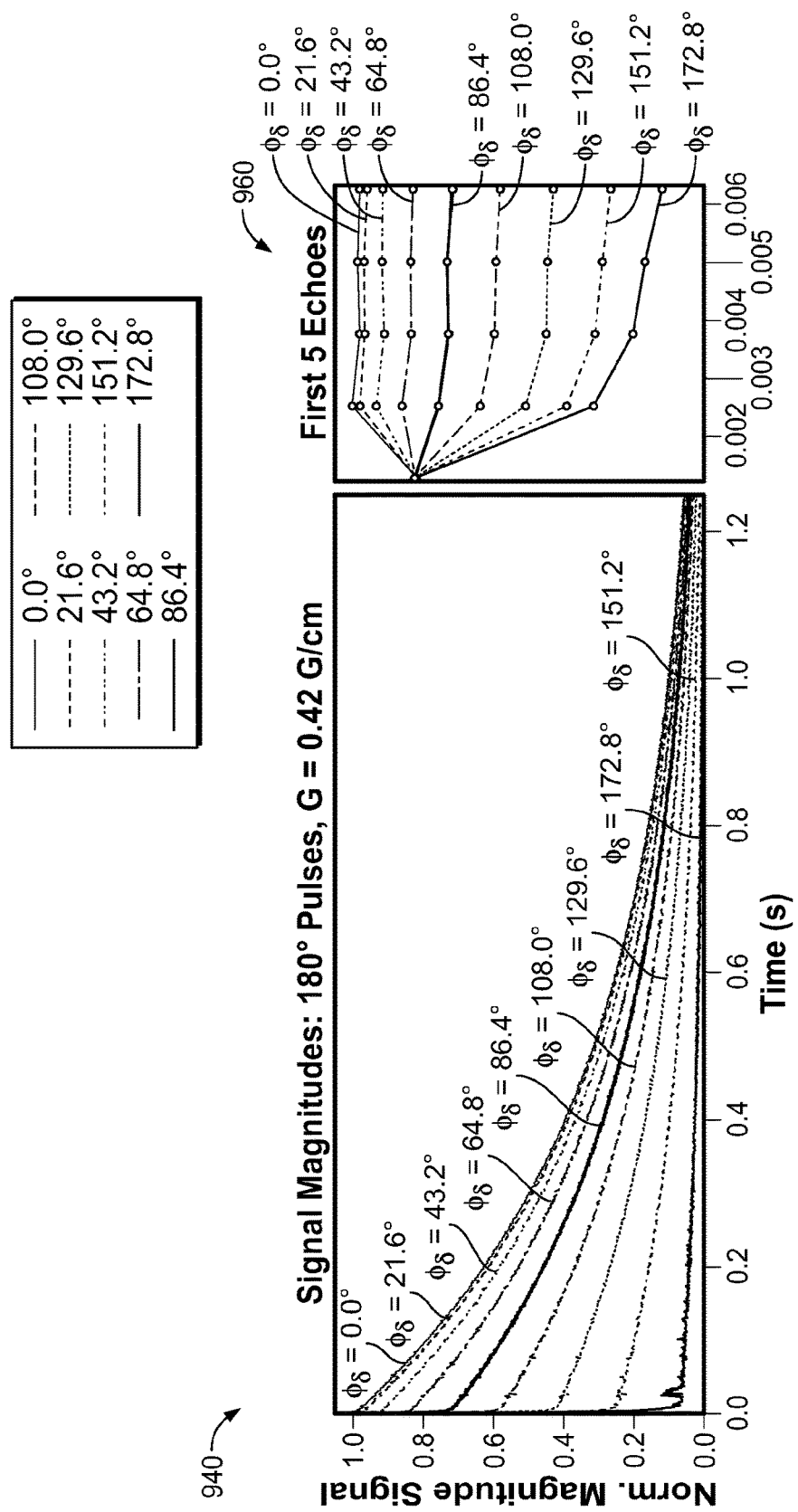

Various values can be used for the phase increment $\phi_\delta$. In some implementations, $\phi_\delta$ is selected based on the degree to which an NMR signal decays as a result of the phase increment. For example, FIGS. 9A-B compare NMR signals induced by a pulse sequence having a single excitation pulse with a tip angle of 90°, and a train of refocusing pulses having a tip angle of 135° (FIG. 9A) or 180° (FIG. 9B) with a phase increment of $\phi_\delta$. As shown in plots 900 and 940, changes in the phase increment $\phi_\delta$ up to approximately 20° does not significantly affect the magnitude of the NMR signal, and has a relatively small effect on the signal other than the introduction of a echo phase oscillation at a frequency $\phi/4\pi\tau$. Referring to plots 920 and 960, the effect on the phase-shifted signal (wherein the receiver phase is made to follow the drift), is that after one or two echoes, some signal is destroyed, then $T_2$ decay occurs as normal afterwards. Accordingly, in some implementations, the phase increment $\phi_\delta$ is a value greater than 0° and approximately less than or equal to 20°. In some implementations, for example when the degradation of the NMR signal is less of a concern, the phase increment $\phi_\delta$ can be greater than 20° (e.g., 30°, 40°, 50°, and so forth).

Figure 10:
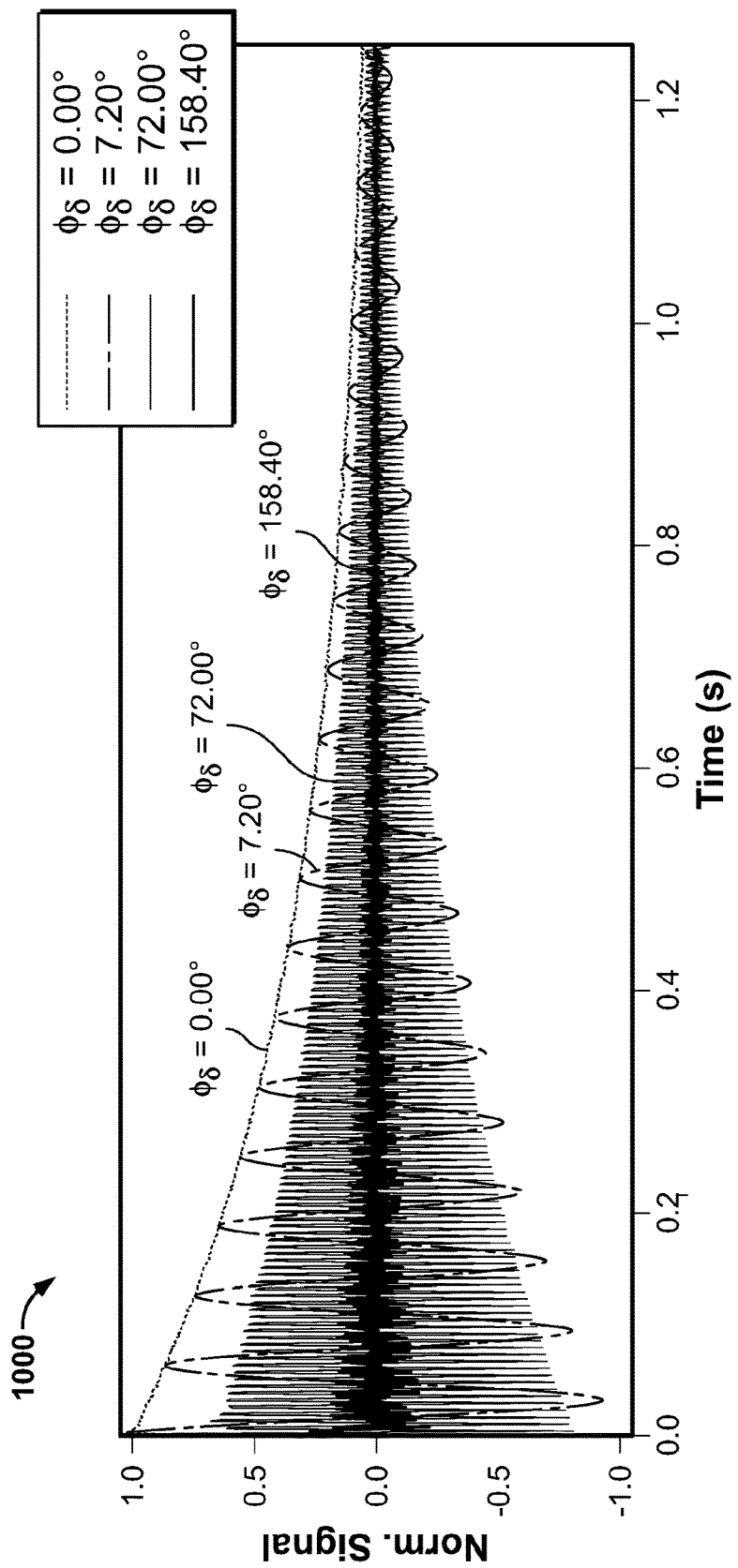
FIG. 10 is a plot that shows example NMR signals acquired using pulse sequences having different phase increments.
Figure 11:
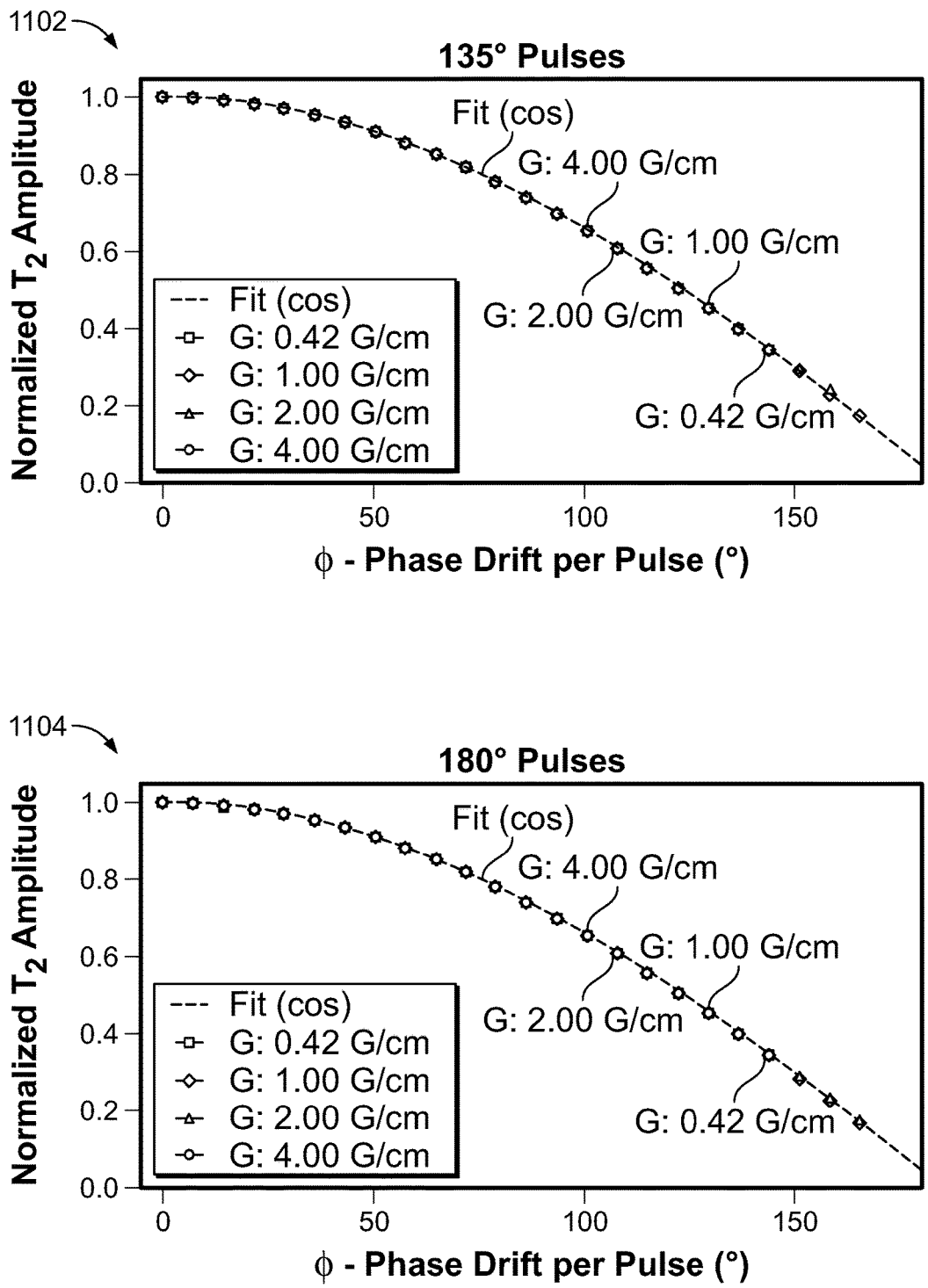
FIG. 11 shows least squares fittings of example NMR signals.

In some implementations, for example in a slice-selective condition, the amount of $T_2$ amplitude destroyed by the inclusion of a phase increment can be relatively independent of both gradient strength and pulse length. For instance, referring to FIG. 10, plot 1000 shows example NMR signals acquired using pulse sequences having different phase increments $\phi_\delta$, where τ is 5 ms. Referring to FIG. 11, least squares fittings of example signals obtained using refocusing pulses having tip angles of either 135° (plot 1102) or 180° (plot 1104) both indicate that the signal strength decays approximately according to cosine. In other implementations, the amount of $T_2$ amplitude destroyed by the inclusion of a phase increment can depend on both gradient strength and pulse length. For example, when the pulse bandwidth is wider than the gradient across the sample, artifacts may be introduced in the event of non-ideal pulse lengths.

Figure 12:
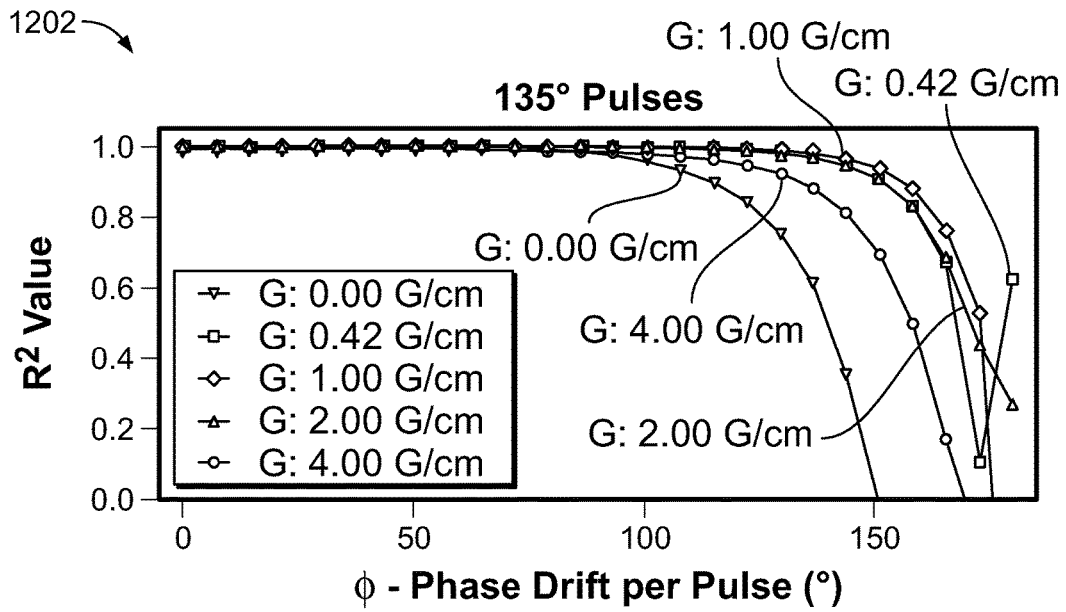
FIG. 12 shows various fittings of $T_2$ amplitude as a function of phase drift.
Figure 12:
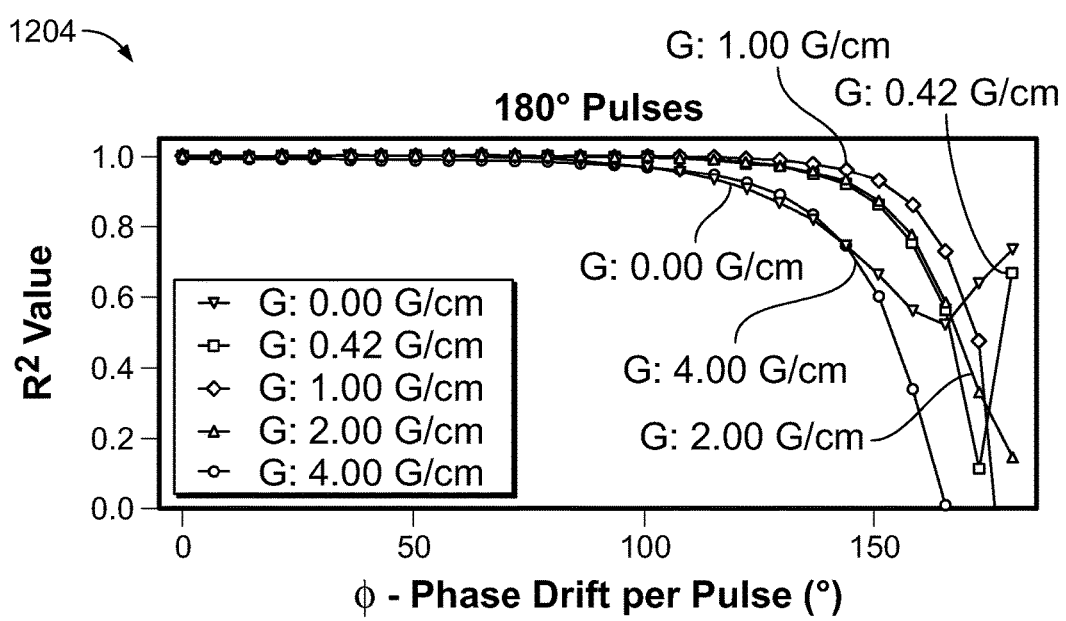
Figure 13:
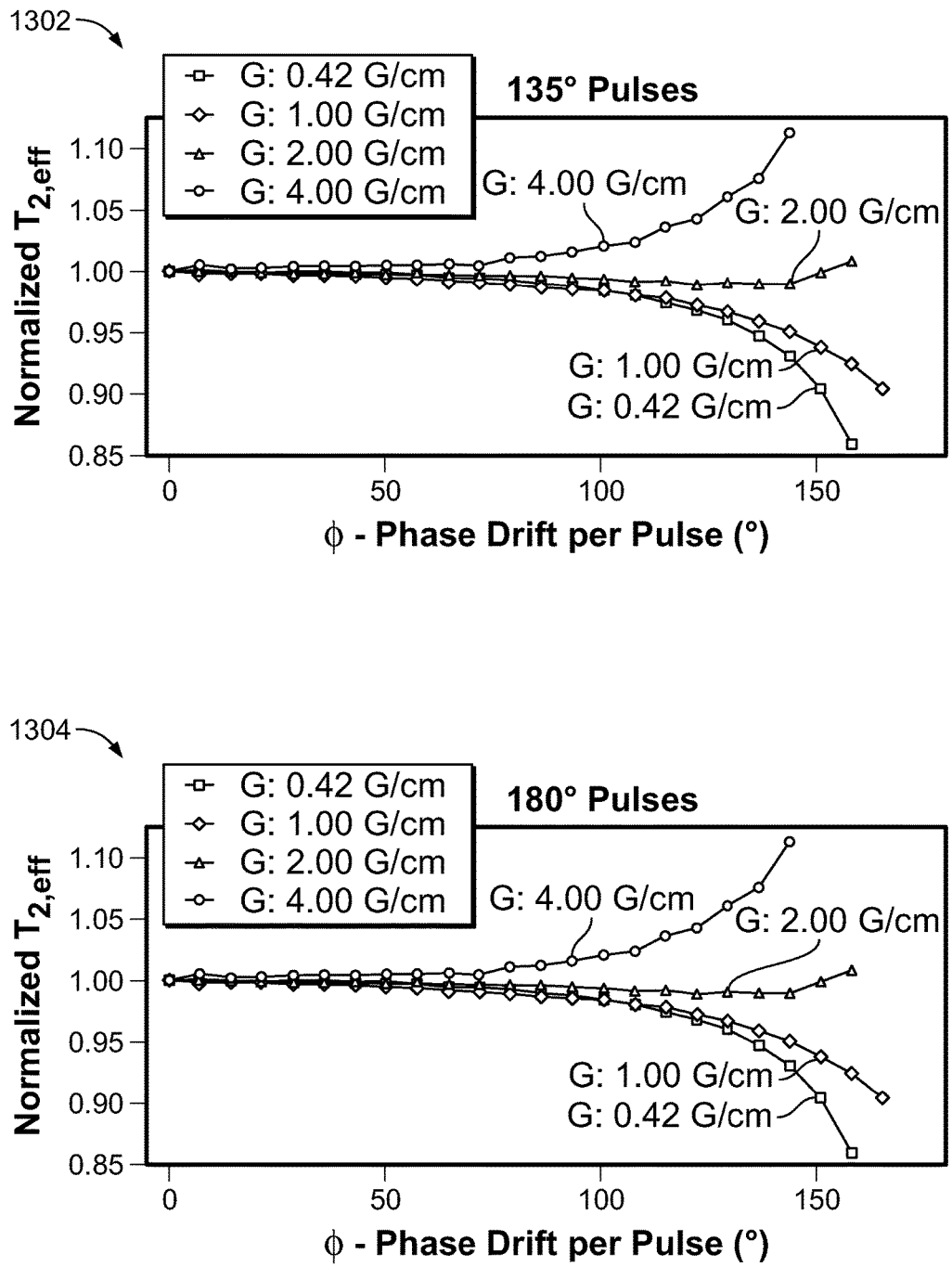
FIG. 13 shows $T_2$ decay rate as a function of phase drift.

Referring to FIG. 12, in some implementations, the coefficient of determination (i.e., $R^2$) values of the $T_2$ fits tend to decay rapidly after approximately 55° for signals obtained using refocusing pulses having tip angles of 135° (plot 1202), and after approximately 100° for signals obtained using refocusing pulses having tip angles of 180° (plot 1204). However, referring to FIG. 13, despite the decay in the amplitude, the fitted $T_2$ decay rate for signals obtained using refocusing pulses having tip angles of either 135° (plot 1302) or 180° (plot 1304) is relatively unchanged as a function of the phase drift, indicating that if the phase drift is known and can be taken into account, $T_2$ measurements are unlikely to be severely distorted by its presence.

Figure 14A:
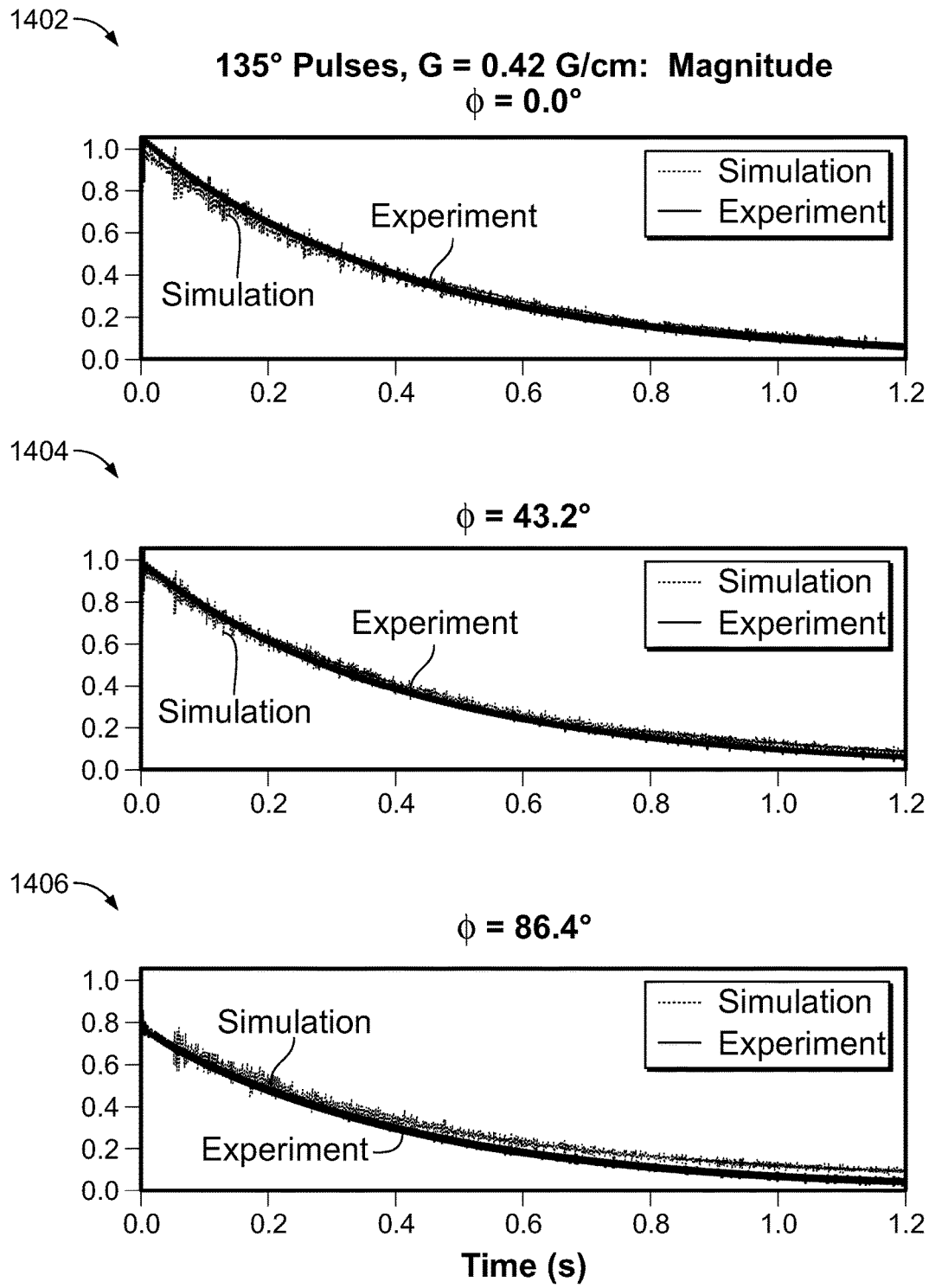
FIGS. 14A-B show comparisons of simulated and experimental echo train magnitudes for 135° pulses and 180° pulses, respectively, in the presence of a magnetic field gradient.
Figure 14B:
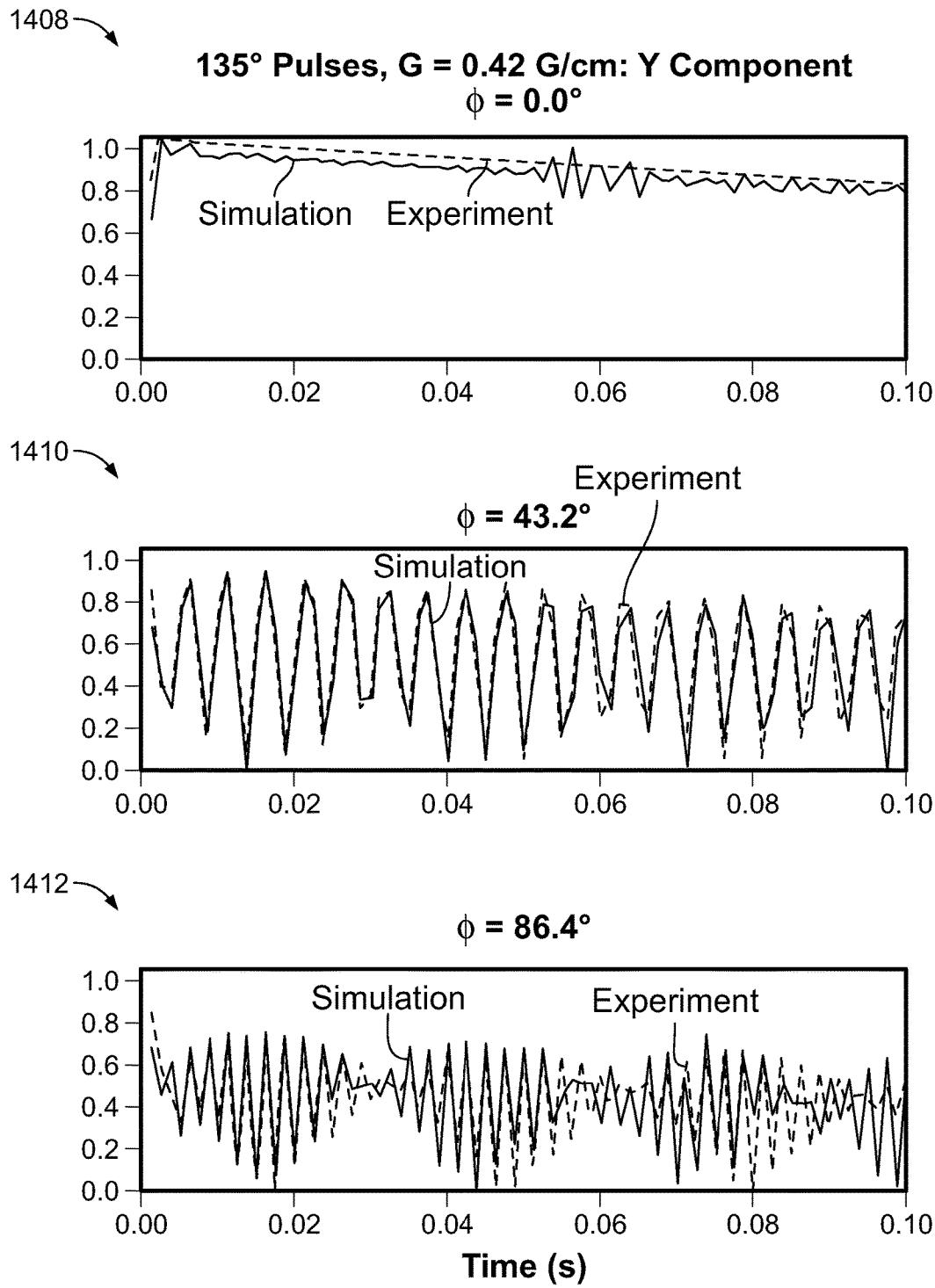
Figure 15:
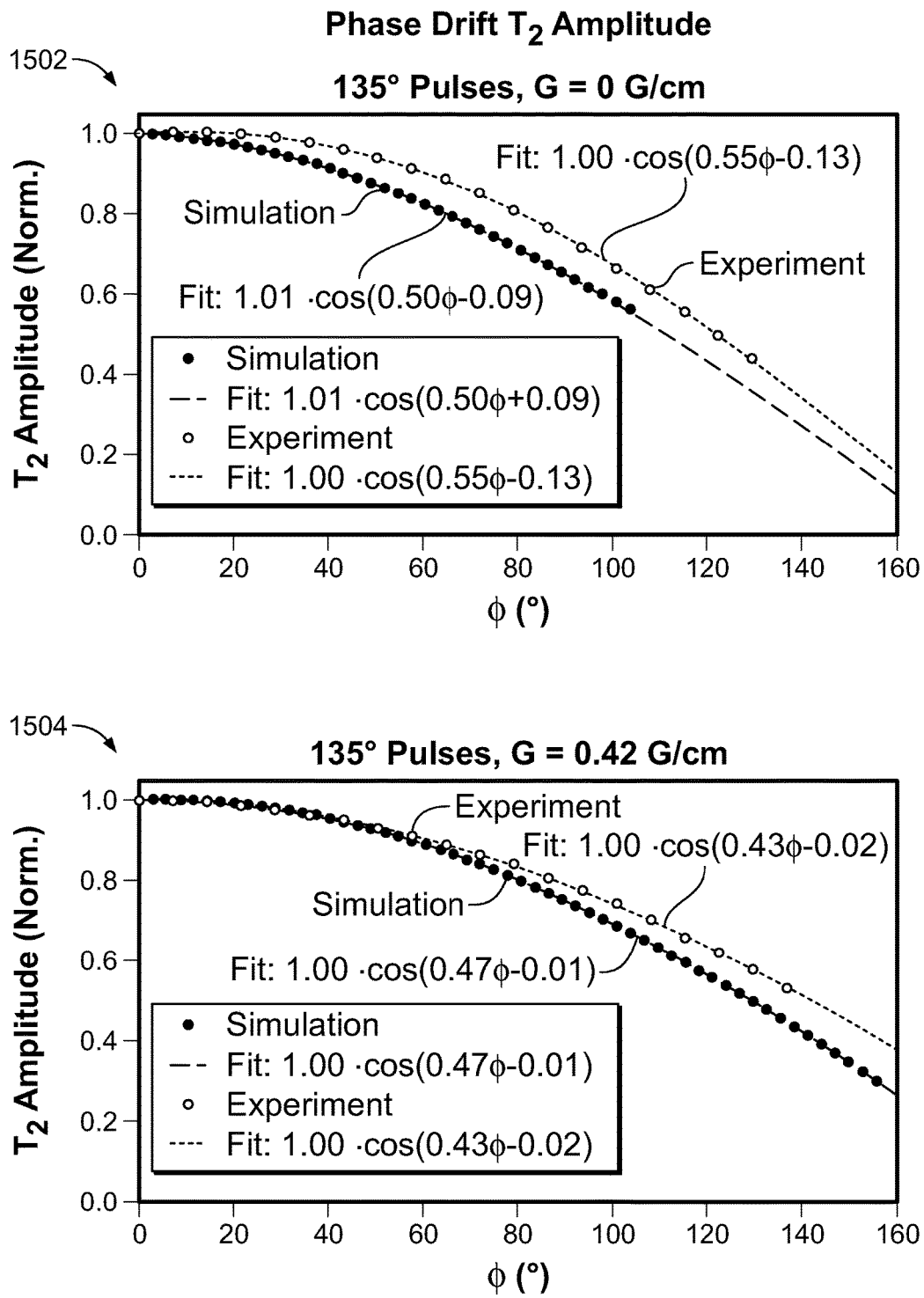
FIG. 15 shows a comparison of simulated and experimental amplitudes of $T_2$ fits as a function of phase drift per pulse.
Figure 15:
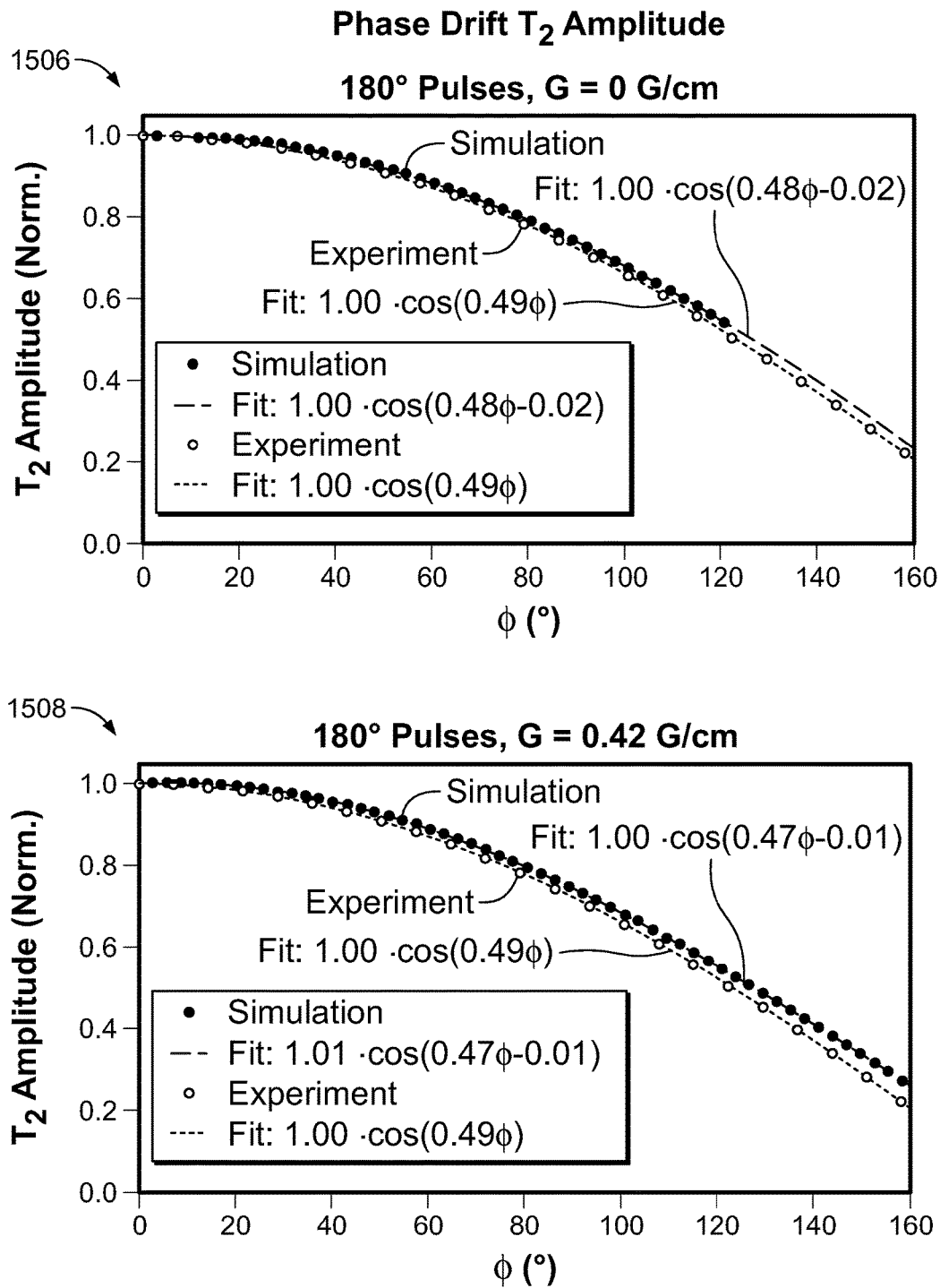

In the above examples, simulated data has been used to illustrate various implementations of single-transient phase cycling. In some implementations, experimental data corresponds fairly well to the simulations, and the two are in good agreement, qualitatively, and primarily differ in the magnitude of the effects. In an example, FIGS. 14A-B show comparisons of various simulated and experimental echo train magnitudes for 135° pulses (plots 1402, 1404, and 1406 of FIG. 14A) and 180° pulses (plots 1408, 1410, and 1412 of FIG. 14B) in the presence of a magnetic field gradient, and plots 1502, 1504, 1506, and 1508 of FIG. 15 show comparisons of various simulated and experimental amplitudes of $T_2$ fits as a function of phase drift per pulse.

In some implementations, phase cycling can used to separate out signals from coupled spins, which will respond to phase according to $\phi^n$, where $\phi$ is the phase and n is a function of the number of coupled spins and the nature of their coupling and can take values n=N−2 k for values k∈$\mathbb{Z}$, [0,N]. In a multi-transient approach, where the phase of the receiver and transmitter are varied according to an appropriate scheme, the number of transients acquired determines the extent of the aliasing, and a sequence selecting phase n will also select at minimum all coherences n+jN where j∈$\mathbb{Z}$, [0,∞]. In a single-transient phase cycling approach, for example an implementation described above, because the phase of the magnetic field B pulses are continuously varied during the sequence, the resolution in the phase-coherence domain is proportional not to the number of transients, but rather to the number of echoes. In some implementations, this can provide an improvement in resolution, for instance an improvement by 2-3 orders of magnitude.

One or more of the above described implementations may provide a variety of benefits. For example, in some implementations, single-transient phase cycling can be performed by inducing a single transient. In contrast, a multi-transient approach may require two or more transients, and thus may require more time to conduct measurements, and may require averaging at multiple positions.

In some implementations, single-transient phase cycling has a very large cycle number, which can correspond to high frequency resolution. In contrast, in some multi-transient methods the resolution may be limited not by the number of pulses but by the number of transients.

In some implementations, single-transient phase cycling may not significantly affect the signal-to-noise ratio of the measurement, and is robust to pulse errors. Accordingly, in some implementations, single-transient phase cycling is suitable for use in a magnetic field gradient.

In some implementations, single-transient phase cycling does not require a moving average, which can remove fast-relaxing components from the measured NMR signals.

In some implementations, the resolution of measurements may be sufficiently high to observe a phase coherence spectrum in a single scan, and does not necessarily average out all but the selected components of the phase coherence spectrum.

In some implementations, single-transient phase cycling is used in combination with existing methods, for instance a phase alternated Carr Purcell (PACP) sequence (e.g., as described in PCT/US2005/020585), for greater artifact cancellation.

A number of implementations have been described. Nevertheless, it will be understood that various modifications may be made without departing from the spirit and scope of the invention. For example, in some implementations, the above described phase incrementing pulse sequences can be used in conjunction with phase-alternating-pair (PAP) methodologies. In an example, implementation, multiple NMR experiments can be conducted with a phase incrementing pulse sequence, as described above, with each experiment having a different set of values for $\phi_A$, $\phi_B$, and $\phi_\delta$. The resulting acquired signals can be averaged together, for example to further remove artifacts and/or to further isolate signal from a single phase coherence order.

Further, while the above examples describe the use of a phase increment in NMR pulse sequences in order to perform single-transient phase cycling, phase increment can also be implemented in electron spin resonance (ESR) pulse sequences. In an example implementation, the use of a phase increment can be used in microwave CPMG pulse sequences in order to provide single-transient phase cycling in ESR applications.

Further still, while the above examples describe the use of single-transient phase cycling in the context of well logging, it should be understood the implementations described here are not limited only to well logging applications, may be broadly applicable to other applications in which NMR or ESR is used to characterize an unknown sample. For example, in some implementations, single-transient phase cycling can be used in other contexts, for instance for medical imaging applications (e.g., magnetic resonance imaging), chemical studies (e.g., NMR or ESR spectroscopy), or other applications of NMR or ESR.

Various aspects of the invention are summarized as follows.

In general, in an aspect, a method for performing magnetic resonance measurements of a sample includes applying an excitation pulse into a volume of polarized spins of a sample, the excitation pulse having a phase of $\phi_A$, applying a sequence of n refocusing pulses, each kth refocusing pulse having a phase $\phi_B+k\phi_\delta$, detecting echoes from the volume induced by each kth refocusing pulse with a receiver phase of $\phi_C$ to determine signal information corresponding on the detected echoes, and determining information about the sample based on the signal information.

Implementations of this aspect may include one or more of the following features:

The sample is can be a subterranean region. The subterranean region can be proximate to a wellbore.

The method can further include applying a static magnetic field in the sample to obtain a volume of polarized nuclear spins.

Phase $\phi_A$ and phase $\phi_B$ can differ by 90°.

$\phi_\delta$ can be determined based on a T2 relaxation time of the volume of the sample. $\phi_\delta$ can be greater than 0° and less than or equal to about 25°.

$\phi_B$ can be equal to D+k*$\phi_\delta$, where D is a fixed constant.

Determining information about the sample can include band pass filtering the signal information.

The band-pass filter can have a width determined based on a T2 component of the signal information.

$\phi_\delta$ can be a fixed constant.

The method can include performing a Fourier transform on the signal information.

The method can include removing information corresponding to artifacts from the signal information.

The method can include separating components of the signal information by phase coherence order.

The method can include obtaining multiple sets of signal information, each set of signal information corresponding to detected echoes associated with different excitation pulse phases, refocusing pulse phases, or receiver phases. The method can include removing artifacts from the sets of signal information by averaging the sets of signal information. The method can include isolating information corresponding to a single phase coherence order by averaging the sets of signal information.

The center of the excitation pulse and the center of a first refocusing pulse in the sequence of refocusing pulses can be separated by a time t.

The center of each refocusing pulse and the center of a corresponding acquisition period for detecting the echoes induced by each refocusing pulse can be separated by a time t.

The center of an acquisition period and a center of a subsequent refocusing pulse can be separated by a time t.

The excitation pulse can have a tip angle of 90°.

Each refocusing pulse can have a tip angle of about 180°. Each refocusing pulse can have a tip angle of about 135°.

The polarized spins can be polarized nuclear spins. The polarized spins can be polarized electron spins.

In general, in another aspect, a system for performing magnetic resonance measurements of a sample includes an antenna module and a data processing module. During use, the antenna module applies an excitation pulse into a volume of polarized nuclear spins of a sample, the excitation pulse having a phase of $\phi_A$, applies a sequence of n refocusing pulses, each kth refocusing pulse having a phase $\phi_B+k\phi_\delta$, and detects echoes from the volume induced by each kth refocusing pulse with a receiver phase of $\phi_C$ to determine signal information corresponding on the detected echoes. During use, the data processing module determines information about the sample based on the signal information.

Implementations of this aspect may include one or more of the following features:

The sample can be a subterranean region. The subterranean region can be proximate to a wellbore.

The system can include a magnet module. During use, the magnet module can apply a static magnetic field in the sample to obtain a volume of polarized nuclear spins.

Phase $\phi_A$ and phase $\phi_B$ can differ by 90°.

$\phi_\delta$ can be determined based on a T2 relaxation time of the volume of the sample.

$\phi_\delta$ can be greater than 0° and less than or equal to about 25°.

$\phi_C$ can be equal to $D+K*\phi_\delta$, where D is a fixed constant.

Determining information about the sample can include band pass filtering the signal information.

The band-pass filter can have a width determined based on a T2 component of the signal information.

$\phi_\delta$ can be a fixed constant.

During operation, the data processing module can perform a Fourier transform on the signal information. During operation, the data processing module can remove information corresponding to artifacts from the signal information. During operation, the data processing module can separate components of the signal information by phase coherence order. During operation, the data processing module can obtain multiple sets of signal information, each set of signal information corresponding to detected echoes associated with different excitation pulse phases, refocusing pulse phases, or receiver phases. During operation, the data processing module can remove artifacts from the sets of signal information by averaging the sets of signal information. During operation, the data processing module can isolate information corresponding to a single phase coherence order by averaging the sets of signal information.

The center of the excitation pulse and the center of a first refocusing pulse in the sequence of refocusing pulses can be separated by a time t.

The center of each refocusing pulse and the center of a corresponding acquisition period for detecting the echoes induced by each refocusing pulse can be separated by a time t.

The center of an acquisition period and a center of a subsequent refocusing pulse can be separated by a time t.

The excitation pulse can have a tip angle of 90°.

Each refocusing pulse can have a tip angle of about 180°. Each refocusing pulse can have a tip angle of about 135°.

The polarized spins can be polarized nuclear spins. The polarized spins can be polarized electron spins.

Other embodiments are within the scope of the following claims.

What is claimed is:

1. A method for performing magnetic resonance measurements of a sample, the method comprising:
   applying an excitation pulse into a volume of polarized spins of a sample, the excitation pulse having a phase of $\varphi_A$;
   applying a sequence of n refocusing pulses, where n>1, each kth refocusing pulse having an incremental phase $\varphi_B+k\varphi_\delta$, wherein k is an index and $\varphi_\delta$ is a constant incremented phase angle;
   detecting echoes from the volume induced by each kth refocusing pulse with a receiver phase of $\varphi_C$ to determine signal information corresponding on the detected echoes, wherein $\varphi_A$, $\varphi_B$, and $\varphi_C$ are different; and
   determining information about the sample based on the signal information.

2. The method of claim 1, wherein phase $\varphi_A$ and phase $\varphi_B$ differ by 90°.

3. The method of claim 1, wherein $\varphi_\delta$ is determined based on a T2 relaxation time of the volume of the sample.

4. The method of claim 1, wherein $\varphi_\delta$ is greater than 0° and less than or equal to approximately 25°.

5. The method of claim 1, wherein $\varphi_C=D+k*\varphi_\delta$, where D is a fixed constant.

6. The method of claim 1, wherein determining information about the sample comprises band pass filtering the signal information.

7. The method of claim 6, wherein band pass filtering the signal information comprises filtering the signal information according to a band-pass filter having a width determined based on a T2 component of the signal information.

8. The method of claim 1, wherein $\varphi_\delta$ is a fixed constant.

9. The method of claim 1, further comprising performing a Fourier transform on the signal information.

10. The method of claim 1, further comprising removing information corresponding to artifacts from the signal information.

11. The method of claim 1, further comprising separating components of the signal information by phase coherence order.

12. The method of claim 1, further comprising obtaining multiple sets of signal information, each set of signal information corresponding to detected echoes associated with different excitation pulse phases, refocusing pulse phases, or receiver phases.

13. The method of claim 12, further comprising removing artifacts from the sets of signal information by averaging the sets of signal information.

14. The method of claim 12, further comprising isolating information corresponding to a single phase coherence order by averaging the sets of signal information.

15. The method of claim 1, wherein a center of the excitation pulse and the center of a first refocusing pulse in the sequence of refocusing pulses are separated by a time t.

16. The method of claim 1, wherein a center of each refocusing pulse and the center of a corresponding acquisition period for detecting the echoes induced by each refocusing pulse are separated by a time t.

17. The method of claim 1, wherein a center of an acquisition period and a center of a subsequent refocusing pulse are separated by a time t.

18. The method of claim 1, wherein the excitation pulse has a tip angle of 90°.

19. The method of claim 1, wherein each refocusing pulse has a tip angle of approximately 180°.

20. The method of claim 1, wherein each refocusing pulse has a tip angle of approximately 135°.

21. The method of claim 1, wherein the polarized spins are polarized nuclear spins.

22. The method of claim 1, wherein the polarized spins are polarized electron spins.

23. System for performing magnetic resonance measurements of a sample, the system comprising:
an antenna module; and
a data processing module;
wherein during use, the antenna module:
applies an excitation pulse into a volume of polarized nuclear spins of a sample, the excitation pulse having a phase of $\varphi_A$;
applies a sequence of n refocusing pulses, where n>1, each kth refocusing pulse having an incremental phase $\varphi_B + k\varphi_\delta$, wherein k is an index and $\varphi_\delta$ is a constant incremented phase angle; and
detects echoes from the volume induced by each kth refocusing pulse with a receiver phase of $\varphi_C$ to determine signal information corresponding on the detected echoes, wherein $\varphi_A$, $\varphi_B$, and $\varphi_C$ are different; and
the data processing module determines information about the sample based on the signal information.

24. The system of claim 23, further comprising a magnet module, wherein during use, the magnet module applies a static magnetic field in the sample to obtain a volume of polarized nuclear spins.

25. The system of claim 23, wherein phase $\varphi_A$ and phase $\varphi_B$ differ by 90°.

26. The system of claim 23, wherein $\varphi_\delta$ is determined based on a T2 relaxation time of the volume of the sample.

27. The system of claim 23, wherein $\varphi_A$ is greater than 0° and less than or equal to approximately 25°.

28. The system of claim 23, wherein $\varphi_C = D + k*\varphi_\delta$, where D is a fixed constant.

29. The system of claim 23, wherein determining information about the sample comprises band pass filtering the signal information.

30. The system of claim 29, wherein band pass filtering the signal information comprises filtering the signal information according to a band-pass filter having a width determined based on a T2 component of the signal information.

31. The system of claim 23, wherein $\varphi_A$ is a fixed constant.

32. The system of claim 23, wherein during operation, the data processing module performs a Fourier transform on the signal information.

33. The system of claim 23, wherein during operation, the data processing module removes information corresponding to artifacts from the signal information.

34. The system of claim 23, wherein during operation, the data processing module separates components of the signal information by phase coherence order.

35. The system of claim 23, wherein during operation, the data processing module obtains multiple sets of signal information, each set of signal information corresponding to detected echoes associated with different excitation pulse phases, refocusing pulse phases, or receiver phases.

36. The system of claim 35, wherein during operation, the data processing module removes artifacts from the sets of signal information by averaging the sets of signal information.

37. The system of claim 35, wherein during operation, the data processing module isolates information corresponding to a single phase coherence order by averaging the sets of signal information.

38. The system of claim 23, wherein a center of the excitation pulse and the center of a first refocusing pulse in the sequence of refocusing pulses are separated by a time t.

39. The system of claim 23, wherein a center of each refocusing pulse and the center of a corresponding acquisition period for detecting the echoes induced by each refocusing pulse are separated by a time t.

40. The system of claim 23, wherein a center of an acquisition period and a center of a subsequent refocusing pulse are separated by a time t.

41. The system of claim 23, wherein the excitation pulse has a tip angle of 90°.

42. The system of claim 23, wherein each refocusing pulse has a tip angle of approximately 180°.

43. The system of claim 23, wherein each refocusing pulse has a tip angle of approximately 135°.

44. The system of claim 23, wherein the polarized spins are polarized nuclear spins.

45. The system of claim 23, wherein the polarized spins are polarized electron spins.

* * * * *

UNITED STATES PATENT AND TRADEMARK OFFICE
CERTIFICATE OF CORRECTION

PATENT NO. : 10,241,172 B2
APPLICATION NO. : 14/780348
DATED : March 26, 2019
INVENTOR(S) : Paul Ganssle and Shriram Sarvotham It is certified that error appears in the above-identified patent and that said Letters Patent is hereby corrected as shown below:

In the Specification

In Column 10, Line 60, delete "$\phi_B$" and insert --$\phi_C$--

In Column 11, Line 52, delete "$\phi_C$ can be equal to $D + K*\phi_\delta$," and insert --$\phi_C$ can be equal to $D + k*\phi_\delta$,--

Signed and Sealed this
Fourth Day of June, 2019

Andrei Iancu
*Director of the United States Patent and Trademark Office*